US008709441B2

(12) United States Patent
Rayner et al.

(10) Patent No.: US 8,709,441 B2
(45) Date of Patent: Apr. 29, 2014

(54) TC-83-DERIVED ALPHAVIRUS VECTORS, PARTICLES AND METHODS

(75) Inventors: Jon O. Rayner, Apex, NC (US); Jonathan F. Smith, Cary, NC (US); Bolyn Hubby, Chapel Hill, NC (US); Elizabeth A. Reap, Durham, NC (US)

(73) Assignee: Alphavax, Inc., Research Triangle Park, NC (US)

(*) Notice: Subject to any disclaimer, the term of this patent is extended or adjusted under 35 U.S.C. 154(b) by 184 days.

(21) Appl. No.: 12/831,017

(22) Filed: Jul. 6, 2010

(65) Prior Publication Data

US 2011/0027306 A1 Feb. 3, 2011

Related U.S. Application Data

(63) Continuation of application No. 11/132,711, filed on May 18, 2005, now abandoned.

(60) Provisional application No. 60/572,212, filed on May 18, 2004.

(51) Int. Cl.
*A61K 39/193* (2006.01)
*A61K 39/295* (2006.01)
*C12N 15/86* (2006.01)

(52) U.S. Cl.
USPC .................. 424/199.1; 424/218.1; 435/320.1

(58) Field of Classification Search
None
See application file for complete search history.

(56) References Cited

U.S. PATENT DOCUMENTS

| | | | |
|---|---|---|---|
| 4,650,764 | A | 3/1987 | Temin et al. |
| 4,708,871 | A | 11/1987 | Geysen |
| 5,091,309 | A | 2/1992 | Schlesinger et al. |
| 5,185,440 | A | 2/1993 | Davies et al. |
| 5,217,879 | A | 6/1993 | Huang et al. |
| 5,505,947 | A | 4/1996 | Johnston et al. |
| 5,639,650 | A | 6/1997 | Johnston et al. |
| 5,643,576 | A | 7/1997 | Johnston et al. |
| 5,703,057 | A | 12/1997 | Johnston et al. |
| 5,726,022 | A | 3/1998 | Burmer |
| 5,739,026 | A | 4/1998 | Garoff et al. |
| 5,766,602 | A | 6/1998 | Xiong et al. |
| 5,789,245 | A | 8/1998 | Dubensky, Jr. et al. |
| 5,792,462 | A | 8/1998 | Johnston et al. |
| 5,811,407 | A | 9/1998 | Johnston et al. |
| 5,814,482 | A | 9/1998 | Dubensky, Jr. et al. |
| 5,827,658 | A | 10/1998 | Liang |
| 5,831,016 | A | 11/1998 | Wang et al. |
| 5,843,723 | A | 12/1998 | Dubensky, Jr. et al. |
| 5,853,719 | A | 12/1998 | Nair et al. |
| 5,958,738 | A | 9/1999 | Lindemann et al. |
| 5,989,553 | A | 11/1999 | Johnston et al. |
| 6,008,035 | A | 12/1999 | Johnston et al. |
| 6,015,686 | A | 1/2000 | Dubensky, Jr. et al. |
| 6,015,694 | A | 1/2000 | Dubensky, Jr. et al. |
| 6,146,874 | A | 11/2000 | Zolotukhin et al. |
| 6,156,558 | A | 12/2000 | Johnston et al. |
| 6,190,666 | B1 | 2/2001 | Garoff et al. |
| 6,194,191 | B1 | 2/2001 | Zhang et al. |
| 6,197,502 | B1 | 3/2001 | Renner et al. |
| 6,224,879 | B1 | 5/2001 | Sjoberg et al. |
| 6,242,259 | B1 | 6/2001 | Polo et al. |
| 6,261,570 | B1 | 7/2001 | Parker et al. |
| 6,267,967 | B1 | 7/2001 | Johnston et al. |
| 6,306,388 | B1 | 10/2001 | Nair et al. |
| 6,329,201 | B1 | 12/2001 | Polo et al. |
| 6,342,372 | B1 | 1/2002 | Dubensky, Jr. et al. |
| 6,376,236 | B1 | 4/2002 | Dubensky, Jr. et al. |
| 6,391,632 | B1 | 5/2002 | Dubensky, Jr. et al. |
| 6,426,196 | B1 | 7/2002 | Dubensky, Jr. et al. |
| 6,451,592 | B1 | 9/2002 | Dubensky, Jr. et al. |
| 6,485,958 | B2 | 11/2002 | Blanche et al. |
| 6,495,143 | B2 | 12/2002 | Lee et al. |
| 6,521,235 | B2 | 2/2003 | Johnston et al. |
| 6,531,135 | B1 | 3/2003 | Johnston et al. |
| 6,583,121 | B1 | 6/2003 | Johnston et al. |
| 6,767,699 | B2 | 7/2004 | Polo et al. |
| 6,770,283 | B1 | 8/2004 | Garoff et al. |
| 6,783,939 | B2 | 8/2004 | Olmsted et al. |
| 7,078,218 | B2 | 7/2006 | Smith et al. |
| 7,419,674 | B2 | 9/2008 | Chulay et al. |
| 2002/0018766 | A1 | 2/2002 | Roberts et al. |
| 2002/0102273 | A1 | 8/2002 | Grieve et al. |
| 2002/0141975 | A1 | 10/2002 | Olmsted et al. |
| 2003/0021766 | A1 | 1/2003 | Vajdy et al. |
| 2003/0091591 | A1 | 5/2003 | Xiong et al. |
| 2003/0119182 | A1 | 6/2003 | Smith et al. |
| 2003/0148262 | A1 | 8/2003 | Polo et al. |
| 2004/0008458 | A1 | 1/2004 | Kase et al. |

(Continued)

FOREIGN PATENT DOCUMENTS

| | | |
|---|---|---|
| WO | 92/10578 | 6/1992 |
| WO | 95/07994 | 3/1995 |

(Continued)

OTHER PUBLICATIONS

Pushko P et al. Replicon-helper systems from attenuated Venezuelan equine encephalitis virus: expression of heterologous genes in vitro and immunization against heterologous pathogens in vivo. Virology. Dec. 22, 1997;239(2):389-401.*

(Continued)

*Primary Examiner* — Mary E Mosher
*Assistant Examiner* — Nick Zou
(74) *Attorney, Agent, or Firm* — Lathrop & Gage LLP

(57) ABSTRACT

The present disclosure provides TC-83 VEE-derived replicons, alphaviral replicon particles and immunogenic compositions containing TC-83 alphaviral replicon particles which direct the expression of at least one antigen when introduced into a suitable host cell. The TC-83 VEE-derived ARPs described herein are improved in that they are subject to a lower vector-specific immune response than prior art ARPs.

7 Claims, 3 Drawing Sheets

(56) References Cited

U.S. PATENT DOCUMENTS

| | | | |
|---|---|---|---|
| 2004/0208848 A1 | 10/2004 | Smith et al. | |
| 2005/0054107 A1 | 3/2005 | Chulay et al. | |
| 2005/0123555 A1 | 6/2005 | Olmsted et al. | |
| 2006/0198854 A1 | 9/2006 | Pushko | |

FOREIGN PATENT DOCUMENTS

| | | |
|---|---|---|
| WO | 95/27044 | 10/1995 |
| WO | 95/31565 | 11/1995 |
| WO | 96/17072 | 6/1996 |
| WO | 96/37220 | 11/1996 |
| WO | 96/37616 | 11/1996 |
| WO | 98/53077 | 11/1998 |
| WO | 99/08706 | 2/1999 |
| WO | 99/51263 | 10/1999 |
| WO | 00/39318 | 7/2000 |
| WO | 00/61772 | 10/2000 |
| WO | 01/12172 | 2/2001 |
| WO | 02/03917 | 1/2002 |
| WO | 02/20721 | 3/2002 |
| WO | 03/023026 A | 3/2003 |
| WO | 2004/085660 | 10/2004 |
| WO | 1751289 B1 | 1/2009 |

OTHER PUBLICATIONS

Johnson BJ et al. Molecular determinants of alphavirus neurovirulence: nucleotide and deduced protein sequence changes during attenuation of Venezuelan equine encephalitis virus. J Gen Virol. Sep. 1986;67 ( Pt 9):1951-60.*

Response to First AU Exam Report, dated Apr. 20, 2011, in Australian Patent Application No. 2005245956, a related application, 6 pp.

Chinese Amended Claims, dated Jun. 19, 2012, in Chinese Patent Application No. 200580024121.9, a related application, 7 pp.

First Indian Office Action, dated Mar. 9, 2012, in Indian Patent Application No. 7516/DELNP/2006, a related application, 1 p.

Japanese First Office Action, dated Jan. 24, 2011, in Japanese Patent Application No. 2007-527482, a related application, 9 pp.

Response to First Japanese Office Action, dated Aug. 1, 2011, in Japanese Patent Application No. 2007-527482, a related application, 10 pp.

Japanese Second Office Action, dated Jan. 6, 2012, in Japanese Patent Application No. 2007-527482, a related application, 5 pp.

Response to Second Japanese Office Action, dated May 10, 2011, in Japanese Patent Application No. 2007-527482, a related application, 11 pp.

Japanese correspondence regarding Notice of Allowance, dated Jul. 12, 2012, in Japanese Patent Application No. 2007-527482, a related application, 4 pp.

Prosecution History of parent application, U.S. Appl. No. 11/132,711, filed May 18, 2005, last item dated Sep. 16, 2010, 92 pages.

International Search Report and Written Opinion in corresponding application PCT/US2005/017766, dated Sep. 21, 2005, 15 pp.

Exam Report in European Application No. 05751967.0, a related application, dated Aug. 20, 2008, 6 pp.

Office Action in European Application No. 05751967.0, a related application, dated Jan. 29, 2008, 5 pp.

Office Action response in European Application No. 05751967.0, a related application, dated May 23, 2008, 32 pp.

Examination Report in Australian Application No. 2005245956, a related application, dated Nov. 11, 2009, 3 pp.

Office Action in Canadian Application No. 2,567,254, a related application, dated Jul. 6, 2010, 3 pp.

Office Action response in Canadian Application No. 2,567,254, a related application, dated Jan. 6, 2011, 7 pp.

Correspondence and first Office Action in Chinese Application No. 200580024121.9, a related application, dated Oct. 24, 2008, 7 pp.

Correspondence and Amended claims response to first Office Action in Chinese Application No. 200580024121.9, a related application, dated Mar. 6, 2009, 8 pp.

Correspondence and second Office Action in Chinese Application No. 200580024121.9, a related application, dated May 8, 2009, 7 pp.

Correspondence and Amended claims response to second Office Action in Chinese Application No. 200580024121.9, a related application, dated Sep. 22, 2009, 16 pp.

Correspondence and third Office Action in Chinese Application No. 200580024121.9, a related application, dated Mar. 9, 2010, 10 pp.

Correspondence and Amended claims response to third Office Action in Chinese Application No. 200580024121.9, a related application, dated Jul. 22, 2010, 8 pp.

Correspondence regarding allowance in Israeli Application No. 178917, a related application, dated Apr. 18, 2010, 64 pp.

Office Action response in Japanese Application No. 2007-527482, a related application, dated Feb. 1, 2011, 9 pp.

International Search Report of International Application Serial No. PCT/US2002/028610 filed Sep. 6, 2002.

International Search Report Corresponding to PCT/US2004/008458 Filed Oct. 25, 2004.

Balasuriya et al. (Feb. 2002) "Alphavirus Replicon Particles Expressing the Two Major Envelope Proteins of Equine Arteritis Virus Induce High Level Protection Against Challenge with Virulent Virus in Vaccinated Horses," *Vaccine* 20:1609-1617.

Barouch et al. (Apr. 2000) "Augmentation of Immune Responses to HIV-1 and Simian Immunodeficiency Virus DNA Vaccines by IL-2/lg Plasmid Administration in Rhesus Monkeys," *Proc. Natl. Acad. Sci. USA* 97(8):4192-4197.

Bell et al. (Mar. 1978) "Effect of Low-NaCl Medium on the Envelope Glycoproteins of Sindbis Virus," *J. Virol.* 25(3):764-769.

Berge et al. (1961) "Attenuation of Venezuelan Equine Encephalo-Myelitis Virus by in Vitro Cultivation in Guinea-Pig Heart Cells," *Am. J. Hyg.* 732:209-218.

Berglund et al. (Aug. 1993) "Semliki Forest Virus Expression System: Production of Conditionally Infectious Recombinant Particles," *Bio/Technology* 11:916-920.

Bernard et al. (Jul. 2000) "Mutations in the E2 Glycoprotein of Venezuelan Equine Encephalitis Virus Confer Heparan Sulfate Interaction, Low Morbidity, and Rapid Clearance from Blood of Mice," *Virology* 276:93-103.

Betts et al. (Nov. 1997) "Cross-Clade Human Immunodeficiency Virus (HIV)-Specific Cytotoxic T-Lymphocyte Responses in HIV-Infected Zambians," *J. Virol.* 71(11):8908-8911.

Bredenbeek et al. (Nov. 1993) "Sindbis Virus Expression Vectors: Packaging of RNA Replicons by Using Defective Helper RNAs," *J. Virol.* 67:6439-6446.

Caley et al. (Apr. 1997) "Humoral, Mucosal, and Cellular Immunity in Response to a Human Immunodeficiency Virus Type 1 Immunogen Expressed by a Venezuelan Equine Encephalitis Virus Vaccine Vector," *J. Virol.* 71(4):3031-3038.

Caley et al. (Mar. 1999) "Venezuelan Equine Encephalitis Virus Vectors Expressing HIV-1 Proteins: Vector Design Strategies for Improved Vaccine Efficacy," *Vaccine* 17:3124-3135.

Casimiro et al. (Jan. 2002) "Vaccine-Induced Immune Responses in Rodents and Nonhuman Primates by Use of a Humanized Immunodeficiency Virus Type 1 Pol Gene," *J. Virol.* 76:185-195.

Chappell et al. (Feb. 2000) "A 9-nt Segment of a Cellular mRNA can Function as an Internal Ribosome Entry Site (IRES) and When Present in Linked Multiple Copies Greatly Enhances IRES Activity," *Proc. Natl. Acad. Sci. USA* 97(4):1536-1541.

Corsini et al. (Sep. 1996) "Efficiency of Transduction by Recombinant Sindbis Replican Virus Varies Among Cell Lines, Including Mosquito Cells and Rat Sensory Neurons," *BioTechniques* 21(3):492-497.

Cutler et al. (Mar. 1986) "Mutants of the Membrane-binding Region of Semliki Forest Virus E2 Protein.I. Cell Surface Transport and Fusogenic Activity," *J. Cell Biol.* 102:889-901.

Czibener et al. (Apr. 2000) "Triatoma Virus Nonstructural Protein Precursor and Capsid Protein Precursor, Genes, Partial cds," GenBank Accession No. AF178440.

Davies et al. (Sep. 1986) "A Single Nucleotide Change in the E2 Glycoprotein Gene of Sindbis Virus Affects Penetration Rate in Cell Culture and Virulence in Neonatal Mice," *Proc. Natl. Acad. Sci. USA* 83:6771.

(56) References Cited

OTHER PUBLICATIONS

Davies et al. (1991) "Attenuating Mutations in the E2 Glycoprotein Gene of Venezuelan Equine Encephalitis Virus; Construction of Single and Multiple Mutants in a Full-Length cDNA Clone," *Virol.* 183:20-31.

Davis et al. (1993) "A Genetically Engineered Live Virus Vaccine for Venezuelan Equine Encephalitis," *J. Cell Biochem.* Supp O No. 17 part D, Abstract N404.

Davis et al. (Jun. 1996) "A Viral Vaccine Vector the Expresses Foreign Genes in Lymph Nodes and Protects Against Mucosal Challenge," *J. Virol.* 70:3781-3787.

Davis et al. (1995) "Attenuated Mutants of Venezuelan Equine Encephalitis Virus Containing Lethal Mutations in the PE2 Cleavage Signal Combined with a Second-Site Suppressor Mutation in E1 ," *Virol.* 212:102-110.

Davis et al. (1996) "Immunization Against Influenza with Attenuated Venezuelan Equine Encephalitis Virus Vectors," In:*Opinions for the Control of Influenza*, L.E.Brown and A.W.Hampson, eds. Elsevier, Amsterdam pp. 803-809.

Davis et al. (1990) "In Vitro Synthesis of Infectious Venezuelan Equine Encephalitis Virus RNS from a cDNA Clone: Analysis of a Viable Deletion Mutant and Mutations Affecting Virulence," *Vaccines* 90:109-113.

Davis et al. (1989) "In Vitro Synthesis of Infectious Venezuelan Equine Encephalitis Virus RNA from a cDNA Clone: Analysis of a Viable Deletion Mutant," *Virol.* 171:189-204.

Davis et al. (1990) "Togaviruses-Alphaviruses," In; *Microbiology*, $4^{th}$ ed., pp. 1049-1057.

Davis et al. (Jan. 2001) "Vaccination of Macaques Against Pathogenic Simian Immunodeficiency Virus with Venezuelan Equine Encephalitis Virus Replication Particles," *J. Virol.* 74(1):371-378.

Davis et al. (1994) "A Molecular Genetic Approach to the Study of Venezuelan Equine Encephalitis Virus Pathogenesis," *Arch. Virol.* 9:99-109.

Davis, Nancy L., et al., "Alphavirus Replicon 16-20 Particles as Candidate HIV Vaccines," IUBMB Life, Taylor and Francis, London, (Apr. 2002) vol. 53 No. 4-5, pp. 209-211.

Dubensky et al. (Jan. 1996) "Sindbis Virus DNA-Based Expression Vectors: Utility for in Vitro and in Vivo Gene Transfer," *J. Virol.* 70:508-519.

Dubuisson et al. (Jun. 1993) "Sindbis Virus Attachment: Isolation and Characterization of Mutants With Impaired Binding to Vertebrate Cells," *J. Virol.* 67:3363-3374.

Favre et al. (1993) "Semliki Forest Virus Capsid Protein Expressed by a Baculovirus Recombinant," *Arch. Virol.* 132:307-319.

Feyzi et al (Oct. 1997) "Structural Requirement of Heparan Sulfate for Interaction with Herpes Simplex Virus Type 1 Virions and Isolated Glycoprotein C," *J. Biol Chem.* 272(40):24850-24857.

Frolov et al. (Oct. 1996) "Alphavirus-Based Expression Vectors: Strategies and Applications," *Proc. Natl. Acad. Sci. USA* 93:11371-11377.

Garoff et al. (Sep. 1983) "Expression of Semliki Forest Virus Proteins from Cloned Complementary DNA. II. The Membrane-Spanning Glycoprotein E2 is Transported to the Cell Surface Without its Normal Cytoplasmic Domain," *J. Cell Biol.* 97:652-658.

Geigenmuller-Gnirke et al. (Apr. 1991) "Complementation Between Sindbis Viral RNAs Produce Infectious Particles with a Bipartite Genome," *Proc. Natl. Acad. Sci. USA.* 88:3253-3257.

Geisbert et al. (May 2002) "Evaluation in Nonhuman Primates of Vaccines against Ebola Virus," *Emerging Infect. Dis.* 8(5):503-507.

Ghosh et al. (Aug. 1999) "Sacbrood Virus Complete Genome," GenBank Accession No. AF092924.

Gingras et al. (May 1996) "Activation of the Translational Suppressor 4E-BP1 Following Infection with Encephalomyocarditis Virus and Poliovirus," *Proc. Natl. Acad. Sci. USA* 93:5578-5583.

Golzio et al. (2002) "Cell Synchronization Effect on Mammalian Cell Permeabilization and Gene Delivery by Electronic Field," *Biochim. Biophys. Acta* 1563:23-28.

Govan et al. (Dec. 2000) "Acute Bee Paralysis Virus, Complete Genome," GenBank Accession No. AF150629.

Gradi et al. (Sep. 1998) "Proteolysis of Human Eukaryotic Translation Initiation Factor eIF4GII, but Not eIF4GI, Coincides with the Shutoff of Host Protein Synthesis after Poliovirus Infection," *Proc. Natl. Acad. Sci. USA* 95:11089-11094.

Grieder et al. (1995) "Specific Restrictions in the Progression of Venezuelan Equine Encephalitis Virus-Induced Disease Resulting from Single Amino Acid Changes in Glycoproteins," *Virol.* 206:994-1006.

Hahn et al. (Apr. 1992) "Infectious Sindbis Virus Transient Expression Vectors for Studying Antigen Processing and Presentation," *Proc. Natl. Acad. Sci. USA* 89:2679-2683.

Heidner et al. (Apr. 1994) "Lethality of PE2 Incorporation into Sindbis Virus can be Suppressed by Second-Site Mutations in E3 and E2," *J. Virol.* 68:2683-2692.

Heise et al. (Jan. 2003) "An Attenuation Mutation in nsP1 of the Sindbis-Group Virus S.A.AR86 Accelerates Nonstructural Protein Processing and Up Regulates Viral 26S RNA Synthesis," *J. Virol.* 77(2):1149-1156.

Heiser et al. (Feb. 2002) "Autologous Dendritic Cells Transfected with Prostate-Specific Antigen RNA Stimulate CTL Responses Against Metastatic Prostate Tumors," *J. Clin. Inv* . 109(3):409-417.

Herweijer et al. (1997) "Self-Amplifying Vectors for Gene Delivery," *Adv. Drug Rev.* 27:5-16.

Hevey et al. (Nov. 2001) "Marburg Virus Vaccines: Comparing Classical and New Approaches," *Vaccine* 20:586-593.

Hevey et al. (1998) "Marburg Virus Vaccines Based upon Alphavirus Replicons Protect Guinea Pigs and Nonhuman Primates," *Virol.* 251(1):28-37.

Hill et al. (Apr. 1997) "RNA-RNA Recombination in Sindbis Virus: Roles of the 3' Conserved Motif, poly(A) Tail, and Nonviral Sequences of Template RNAs in Polymerase Recognition and Template Switching," *J. Virol.* 71:2693-2704.

Hirsch et al. (Jun. 1996) "Patterns of Viral Replication Correlate with Outcome in Simian Immunodeficiency Virus (SIV)-Infected Macaques: Effect of Prior Immunization with a Trivalent SIV Vaccine in Modified Vaccinia Virus Ankara," *J. Virol.* 70(6):3741-3752.

Hodgson et al. (1993) "Expression of Venezuelan Equine Encephalitis Viral Proteins by Recombinant Baculoviruses," *Am. J. Trop. Med. Hygiene* 49:195-196.

Holcik et al. (Jul. 2000) "Functional Characterization of the X-Linked Inhibitor of Apoptosis (XIAP) Internal Ribosome Entry Site Element: Role of La Autoantigen in XIAP Translation," *Mol. Cell. Biol.* 20(13):4648-4657.

Holcik et al. (Jul. 1999) "A New Internal-Ribosome-Entry-Site Motif Potentiates XIAP-Mediated Cytoprotection," *Nature Cell Biol.* 1:190-192.

Holcik et al. (Jan. 2003) "The Internal Ribosome Entry Site-Mediated Translation of Antiapoptotic Protein XIAP is Modulated by the Heterogeneous Nuclear Ribonucleoproteins C1 and C2," *Mol. Cell. Biol.* 23(1):280-288.

Isawa et al. (Apr. 1998) "Infectious Flacherie Virus Genomic RNA, Complete Sequence," GenBank Accession No. AB000906.

Jalanko (Jul. 1985) "Expression of Semliki Forest Virus Capsid Protein from SV40 Recombinant Virus," *FEBS Lett.* 186:59-64.

Jang et al. (1990) "Cap-Independent Translation of Encephalomyocarditis Virus RNA: Structural Elements of the Internal Ribosomal Entry Site and Involvement of a Cellular 57kD RNA-Binding Protein," *Genes and Development* 4:1560-1572.

Joachims et al. (Jan. 1999) "Cleavage of Poly(A)-Binding Protein by Enterovirus Proteases Concurrent with Inhibition of Translation In Vitro," *J. Virol.* 73(1):718-727.

Johnson et al. (Feb. 1998) "*Drosophilia* C Virus Strain EB, Complete Genome," GenBank Accession No. AF014388.

Johnston et al. (1996) "Alphaviruses,", In: *Fields Virology*, $3^{rd}$ ed., Lippincott-Raven Publishers, Philadelphia, Chapt, 28:843-898.

Johnston et al. (1988) "Selection for Accelerated Penetration in Cell Culture Coselects for Attenuated Mutants of Venezuelan Equine Encephalitis Virus," *Virol.* 162:437-443.

Kinney et al. (Mar. 1993) "Attenuation of Venezuelan Equine Encephalitis Virus Strain TC-83 Is Encoded by the 5"-Noncoding Region and the E2 Envelope Glycoprotein," *J. Virol.* 67:1269-1277.

(56) References Cited

OTHER PUBLICATIONS

Kinney et al. (1989) "The Full Length Nucleotide Sequences of the Virulent Trinidad Donkey Strain of Venezuelan Equine Encephalitis Virus and Its Attenuated Vaccine Derivative, Strain TC-83," *Virology* 170:19-30.
Klimstra et al. (Sep. 1998) "Adaptation of Sindbis Virus to BHK Cells Selects for Use of Heparan Sulfate as an Attachment Receptor," *J. Virol* 72:7357-7366.
Knight (1999) "Secretion from Bovine Chromaffin Cells Acutely Expressing Exogenous Proteins using a Recombinant Semliki Forest Virus Containing an EGFP Reporter," *Mol. Cell. Neuro.* 14(6):486-505.
Kohl et al. (1999) "Transient Gene Expression in Mammalian and Mosquito Cells Using a Recombinant Semliki Forest Virus Expressing T7 RNA Polymerase," *Appl. Microbiol. Biotechnol.* 53(1):51-56.
Koller et al. (Sep. 2001) "A High-Throughput Alphavirus-Based Expression Cloning System for Mammalian Cells," *Nature Biotech.* 19:851-855.
Kondor-Koch et al. (Sep. 1983) "Expression of Semliki Forest Virus Proteins from Cloned Complementary DNA. I. The Fusion Activity of the Spike Glycoprotein," *J. Cell. Biol.* 97(3):644-651.
Kumamoto et al. (Jan. 2002) "Induction of Tumor-Specific Protective Immunity by in situ Langerhans Cell Vaccine," *Nature Biotech.* 20:64-69.
Leat et al. (Aug. 2000) "Black Queen Cell Virus Nonstructural Polyprotein (orf1) and Structural Polyprotein (orf2) Genes, Complete Cds," GenBank Accession No. AF183905.
Lee et al. (1997) "Efficient Long-Term Coexpression of a Hammerhead Ribozyme Targeted to the U5 Region of HIV-1 LTR by Linkage to the Multidrug-Resistance Gene," *Antisense & Nucleic Acid Drug Development* 7:511-522.
Lemm et al. (1994) "Polypeptide Requirements for Assembly of Functional Sindbis Virus Replication Complexes: A Model for the Temporal Regulation of Minus-and Plus-Strand RNA Synthesis," *EMBO J.* 13:2925-2934.
Leone et al. (1985) "In Vitro Synthesis of the Gene Coding for the Glycoprotein E1 of Sindbis Virus," *Microbiologica* 8(2):123-130.
Li et al. (1996) "Production of Infectious Recombinant Moloney Murine Leukemia Virus Particles in BHK Cells Using Semliki Forest Virus-Derived RNA Expression Vectors," *Proc. Natl. Acad. Sci. USA* 93:11658-11663.
Liljestrom et al. (Dec. 1991) "A New Generation of Animal Cell Expression Vectors Based on the Semliki Forest Virus Replicon." *BioTechnology* 9:1356-1361.
Liljestrom (1994) "Alphavirus Expression Systems," *Curr. Opin. Biotechnol.* 5:495-500.
Liljestrom et al. (Aug. 1991) "In Vitro Mutagenesis of a Full-Length cDNA Clone of Semliki Forest Virus: The Small 6,000-Molecular-Weight Membrane Protein Modulates Virus Release," *J. Virol.* 65:4107-4113.
Lu et al. (2001) "Transmission of Replication-Defective Sindbis Helper Vectors Encoding Capsid and Envelope Proteins," *J. Virol. Methods* 91(1):59-65.
Lobigs et al. (Mar. 1990) "Fusion Function of the Semliki Forest Virus Spike is Activated by Proteolyic Cleavage of the Envelope Glycoprotein Precursor p62," *J. Virol.* 64:1233-1240.
Ludwig et al. (1996) "A Putative Receptor for Venezuelan Equine Encephalitis Virus from Mosquito Cells," Journal of Virology 70(8):5592-5599.
Ludwig et al. (2001) "Comparative Neurovirulence of Attenuated and Non-Attenuated Strains of Venezuelan Equine Encephalitis Virus in Mice," *Am. J. Trop. Med. Hyg.* 64(1-2):49-55.
Lundstrom et al. (1985) "Secretion of Semliki Forest Virus Membrane Glycoprotein E1 from *Bacillus subtilis*," *Virus Res.* 2:69-83.
MacDonald et al. (Jan. 2000) "Role of Dendritic Cell Targeting in Venezuelan Equine Encephalitis Virus Pathogenesis," *J. Virol.* 74(2):914-922.
Martinez-Salas et al. (May 2001) "Functional Interactions in Internal Translation Initiation Directed by Viral and Cellular IRES Elements," *J. Gen. Virol.* 82:973-984.
McKnight et al. (Mar. 1996) "Deduced Consensus Sequence of Sindbis Virus Strain AR339: Mutations Contained in Laboratory Strains which Affect Cell Culture and In Vivo Phenotypes," *J. Virol.* 70(3):1981-1989.
Melancon et al. (May 1987) "Processing of the Semliki Forest Virus Structural Polyprotein: Role of Capsid Protease," *J. Virol.* 61:1301-1309.
Melancon et al. (1986) "Reinitiation of Translocation in the Semliki Forest Virus Structural Polyprotein: Identification of the Signal for the E1 Glycoprotein," *EMBO J.* 5:1551-1560.
Moon et al. (Dec. 1998) "Hopalosiphum padi Virus Complete Genome," GenBank Accession No. AF022937.
Morgenstern et al. (1990) "Advanced Mammalian Gene Transfer: High Titre Retroviral Vectors with Multiple Drug Selection Markers and a Complementary Helper-Free Packaging Cell Line," *Nuc. Acid. Res.* 18:3587-3596.
Nakashima et al. (Jan. 1999) "Himetobi P Virus Genomic RNA, Complete Sequence," GenBank Accession No. AB017037.
Oker-Blom et al. (Mar. 1989) "Expression of Sindbis Virus 26S cDNA in *Spodoptera frugiperda* (Sf9) Cells, Using a Baculovirus Expression Vector," *J. Virol.* 63:1256-1264.
Olmsted et al. (1986) "Characterization of Sindbis Virus Epitopes Important for Penetration in Cell Culture and Pathogenesis in Animals," *Virology* 148:245-254.
Orkin et al. (Dec. 1995) "Report and Recommendations of the Panel to Assess the NIH Investment in Research on Gene Therapy," http://www.nih.gov/news/panelrep.html, pp. 1-39.
Paredes et al. (Oct. 1993) "Three-Dimensional Structure of a Membrane-Containing Virus," *Proc. Natl. Acad. Sci. USA* 90:9095-9099.
Paessler et al., (Sep. 2003) "Recombinant sindbis/Venezuelan equine encephalitis virus is highly attenuated and immunogenic", J. Virol. 77(17):9278-9286.
Pierce et al. (1974) "Effect of Ionic Strength on the Binding of Sindbis Virus to Chick Cells," Journal of Virology 13(5):1030-1036.
Pittman et al. (1996) "Long-Term Duration of Detectable Neutralizing Antibodies after Administration of Live-Attenuated VEE Vaccine and Following Booster Vaccination with Inactivated VEE Vaccine," *Vaccine* 14(4):337-343.
Polo et al. (Sep. 1990) "Attenuating Mutations in Glycoproteins E1 and E2 of Sindbis Virus Produces a Highly Attenuated Strain When Combined in Vitro," *J. Virol.* 64:4438-4444.
Pratt et al. (2003) "Genetically Engineered Live Attenuated Vaccines for Venezuelan Equine Encephalitis: Testing in Animal Models," *Vaccine* 21(25-26):3854-3862.
Presley et al. (Apr. 1991) "Proteolytic Processing of the Sindbis Virus Membrane Protein Precursor PE2 is Nonessential for Growth in Vertebrate Cells but is required for Efficient Growth in Invertebrate Cells," *J. Virol.* 65:1905-1909.
Pugachev et al. (Nov. 2000) "Development of a Rubella Virus Vaccine Expression Vector: Use of a Picornavirus Internal Ribosome Entry Site Increases Stability of Expression," *J. Virol.* 74:10811-10815.
Pushko et al. (1997) "Replicon-Helper Systems from Attenuated Venezuelan Equine Encephalitis Virus: Expression of Heterologous Genes in Vitro and Immunization Against Heterologous Pathogens in Vivo," *Virol.* 239:389-401.
Pushko et al. (2001) "Recombinant RNA Replicons Derived from Attenuated Venezuelan Equine Encephalitis Virus Protect Guinea Pigs and Mice from Ebola Hemorrhagic Fever Virus," *Vaccine* 19:142-153.
Pushko et al. (2001) "Individual and Bivalent Vaccines Based on Alphavirus Replicons Protect Guinea Pigs Against Infection with Lassa and Ebola Viruses," Journal of Virology, The American Society for Microbiology U.S. 75(23):11677-11685.
Rayner et al. (Sep. 2002) "Alphavirus Vectors and Vaccination," *Rev. Med. Virol.* 12(5):279-296.
Rice et al. (Oct. 1985) "Expression of Sindbis Virus Structural Proteins via Recombinant Vaccinia Virus: Synthesis, Processing, and Incorporation into Mature Sindbis Virions," *J. Virol.* 56:227-239.
Riedel (Apr. 1985) "Different Membrane Anchors Allow the Semliki Forest Virus Spike Subunit E2 to Reach the Cell Surface," *J. Virol.* 54:224-228.

(56) References Cited

OTHER PUBLICATIONS

Roberts et al. (1997) “Complementation of Defective Picornavirus Internal Ribosome Entry Site (IRES) Elements by the Coexpression of Fragments of the IRES,” *Virol.* 227:53-62.
Rota et al. (Oct. 2003) “SARS Coronavirus Urbani, Complete Genome,” GenBank Accession No. AY278741.
Rosenberg, S.A. (Mar. 1999) “A New Era for Cancer Immunotherapy Based on the Genes that Encode Cancer Antigens,” *Immunity* 10:281-287.
Russell et al. (Apr. 1989) “Sindbis Virus Mutations Which Coordinately Affect Glycoprotein Processing, Penetration, and Virulence in Mice,” *j. Virol.* 63:1619-1629.
Salminen et al. (Jan. 1992) “Membrane Fusion Process of Semliki Forest Virus II: Cleavage-Dependant Reorganization of the Spike Protein Complex Controls Virus Entry,” *J. Cell. Biol.* 116:349-357.
Scherer et al. (1972) “Observations of Equines, Humans and Domestic and Wild Vertebrates During the 1969 Equine Epizootic and Epidemic of Venezuelan Encephalitis in Guatemala,” American Journal of Epidemiology 95(3):255-266.
Schlesinger et al. (1996) “*Togaviridae*: The Viruses and Their Replication,” In: *Fields Virology*, 3$^{rd}$ Edition, Lipincott-Raven Publishers, Philadelphia, pp. 825-841.
Schlesinger (Jan. 1993) “Alphaviruses-Vectors for the Expression of Heterologous Genes,” *TIBTech* 11:18-22.
Schlesinger (1986) Defective RNAs of Alphaviruses, In; *The Togaviridae and Flaviviridae*, Plenum Publishing Corp., New York, pp. 149-169.
Schoepp et al. (1993) “Directed Mutagenesis of a Sindbis Virus Pathogenesis Site,” *Virol.* 193:149-159.
Shi et al. (2002) “Construction and Characterization of Subgenomic Replicons of New York Strain of West Nile Virus,” *Virol.* 296(2):219-233.
Simpson et al. (1996) “Complete Nucleotide Sequence and Full Length cDNA Clone of S.A.Ar86, a South African Alphavirus Related to Sindbis,” *Virol.* 222:464-469.
Sjoberg et al. (Nov. 1994) “A Significantly Improved Semliki Forest Virus Expression System Based on Translation Enhancer Segments from the Viral Capsid Gene,” *BioTechnol.* 12:1127-1131.
Smerdou et al. (Feb. 1999) “Two-Helper RNA System for Production of Recombinant Semliki Forest Virus Particles,” *J. Virol.* 73(2):1092-1098.
Spotts et al. (Dec. 1998) “Resistance to Alpha/Beta Interferons Correlates with the Epizootic and Virulence Potential of Venezuelan Equine Encephalitis Viruses and is Determined by the 5' Noncoding Region and Glycoproteins,” *J. Virol.* 72:10286-10291.
Strauss et al. (1990) “Alphavirus Proteinases,” *Sem. Virol.* 1:347-356.
Strauss et al. (Sep. 1994) “The Alphaviruses: Gene Expression, Replication, and Evolution,” *Microbiological Rev.* 58:491-562.
Suomalainen et al. (Aug. 1992) “Spike Protein-Nucleocapsid Interactions Drive the Budding of Alphaviruses,” *J. Virol.* 66(8):4737-4747.
Sykes et al. (1999) “Genetic Live Vaccines Mimic the Antigenicity but Not Pathogenicity of Live Viruses,” *DNA Cell Biol.* 18(7):521-531.
Thompson et al. (Oct. 2003) “Enterovirus 71 Contains a Type I IRES Element that Functions When Eukaryotic Initiation Factor eIF4G is Cleaved,” *Virol.* 315:259-266.
Ubol et al. (May 1994) “Neurovirulent Strains of Alphavirus Induce Apoptosis in bcl-2-Expressing Cells: Role of a Single Amino Acid Change in the E2 Glycoprotein,” *Proc. Natl. Acad. Sci. USA* 91:5202-5206.
Van Der Velden et al. (1995) “Defective Point Mutants of the Encephalomyocarditis Virus Internal Ribosome Entry Site can be Complemented in Trans,” *Virol.* 214:82-90.
Van Der Wilk et al. (Dec. 1997) “Acyrthosiphon Pisum Virus Protein P1 Gene, Complete cds; and Protein P2 Gene, Partial cds,” GenBank Accession No. AF024514.
Verma et al. (Sep. 1997) “Gene Therapy—Promise and Prospects,” *Nature* 389:239-242.
Waite et al. (Jan. 1970) “Inhibition of Sindbis Virus Production by Media of Low Ionic Strength: Intacellular Events and Requirements for Reversal” *J. Virol.* 5:60-71.
Walton et al. (1972) “Epizootic Venezuelan Equine Enchephalomyelitis in Central America. Disease Pattern and Vaccine Evaluation in Nicaragua, 1969-1970,” *Am. J. Epidemiol.* 95:247-254.
Wang et al. (Dec. 2000) “Core Protein-Coding Sequence, But Not Core Protein, Modulates the Efficiency of Cap-Independent Translation Directed by the Internal Ribosome Entry Site of Hepatitus C Virus,” *J. Virol.* 74(23):11347-11358.
Ward et al. (Jun. 2002) “Immunotherapeutic Potential of Whole Tumor Cells,” *Cancer Immunol. Immunother.* 51:351-357.
Weiss et al. (Aug. 1991) “Recombination Between Sindbis Virus RNAs,” *J. Virol.* 65:4017-4025.
Wen et al. (1986) “Expression of Genes Encoding Vesicular Stomatitis and Sindbis Virus Glycoproteins in Yeast Leads to Formation of Disulfide-Linked Oligomers,” *Virol.* 153:150-154.
Wen et al. (2001) “Tricistronic Viral Vectors Co-Expressing Interleukin-12 (IL-12) and CD80 (B7-1) for the Immunotherapy of Cancer: Preclinical Studies in Myeloma,” *Cancer Gene Therapy* 8(5):361-370.
White et al. (Apr. 2001) “Role of Alpha/Beta Interferon in Venezuelan Equine Encephalitis Virus Pathogenesis: Effect of an Attenuating Mutation in the 5' Untranslated Region,” *J. Virol.* 75:3706-3718.
Williamson et al. (Feb. 2003) “Characterization and Selection of HIV-1 Subtype C Isolates for Use in Vaccine Development,” *AIDS Research and Human Retroviruses* 19(2):133-144.
Wilson et al. (Jul. 2000) “Naturally Occurring Dicistronic Cricket Paralysis Virus RNA is Regulated by Two Internal Ribosome Entry Sites,” *Mol. Cell. Biol.* 20(14):4990-4999.
Wilson et al. (Jul. 2001) “Vaccine Potential of Ebola Virus VP24, VP30, VP35, and VP40 Proteins,” *Virology* 286:384-390.
Wilson et al. (Jul. 2000) “Cricket Paralysis Virus NonStructural Polyprotein and Structural Polyprotein Genes, Complete cds,” GenBank Accession No. AF218039.
Xiong et al. (Mar. 1989) “Sindbis Virus: An Efficient, Broad Host Range Vector for Gene Expression in Animal Cells,” *Science* 243:1188-1191.
Yamanaka et al. (Sep. 2002) “Marked Enhancement of Antitumor Immune Responses in Mouse Brain Tumor Models by Genetically Modified Dendritic Cells Producing Semliki Forest Virus-Mediated Interleukin-12,” *J. Neurosurg.* 97:611-618.
Yamanaka et al. (Mar. 2001) “Enhancement of Antitumor Immune Response in Glioma Models in Mice by Genetically Modified Dendritic Cells Pulsed with Semliki Forest Virus-Mediated Complementary DNA,” *J. Neurosurg.* 94:474-481.
Yang et al. (1997) “Location of the Internal Ribosome Entry Site in the 5'Non-Coding Region of the Immunoglobulin Heavy-Chain Binding Protein (BiP) mRNA: Evidence for Specific RNA-Protein Interactions,” *Nuc. Acids. Res.* 25(14):2800-2807.
Ying et al. (Jul. 1999) “Cancer Therapy Using a Self-Replicating RNA Vaccine,” *Nature Medicine* 5(7):823-827.
Zhao et al. (Dec. 1992) “Role of Cell Surface Spikes in Alphavirus Budding,” *J. Virol.* 66:7089-7095.

* cited by examiner

SEQUENCE LISTING

```
<160> NUMBER OF SEQ ID NOS: 5

<210> SEQ ID NO 1
<211> LENGTH: 342
<212> TYPE: DNA
<213> ORGANISM: Artificial sequence
<220> FEATURE:
<223> OTHER INFORMATION: Synthetic construct:  cloned DNA fragment to
      insure proper translational control.

<400> SEQUENCE: 1

ctattccaga agtagtgagg aggctttttt ggaggcctag gcttttgcaa aaagcttgta      60

tatccatttt cggatctgat caagagacag gatgaggatc gtttcgcatg attgaacaag     120

atggattgca cgcaggttct ccggccgctt gggtggagag gctattcggc tatgactggg     180

cacaacagac aatcggctgc tctgatgccg ccgtgttccg gctgtcagcg caggggcgcc     240

cggttctttt tgtcaagacc gacctgtccg gtgccctgaa tgaactgcag gacgaggcag     300

cgcggctatc gtggctggcc acgacgggcg ttccttgcgc ag                        342


<210> SEQ ID NO 2
<211> LENGTH: 33
<212> TYPE: DNA
<213> ORGANISM: Artificial sequence
<220> FEATURE:
<223> OTHER INFORMATION: Synthetic construct:  Oligonucleotide useful as
      a primer.

<400> SEQUENCE: 2

gccttgcgga tcatgctgaa gcatataaag cgc                                   33


<210> SEQ ID NO 3
<211> LENGTH: 33
<212> TYPE: DNA
<213> ORGANISM: Artificial sequence
<220> FEATURE:
<223> OTHER INFORMATION: Synthetic construct:  Oligonucleotide useful a
      as a primer.

<400> SEQUENCE: 3

gcgctttata tgcttcagca tgatccgcaa ggc                                   33


<210> SEQ ID NO 4
<211> LENGTH: 2931
<212> TYPE: DNA
<213> ORGANISM: Artificial sequence
<220> FEATURE:
```

<223> OTHER INFORMATION: Synthetic construct: Western equine encephalitis virus cassette.

<400> SEQUENCE: 4

```
tcactagtta cagcgctgtg cgtgctttcg aatgtcacat tcccttgcga caaaccaccc     60
gtgtgctatt cactggcgcc agaacgaaca ctcgacgtgc tcgaggagaa cgtcgacaat    120
ccaaattacg acacgctgct ggagaacgtc ttgaaatgtc catcacgccg gcccaaacga    180
agcattaccg atgacttcac gctgaccagt ccctacctgg ggttctgccc gtattgcaga    240
cactcagcgc catgttttag cccaataaaa attgagaacg tgtgggacga atctgatgat    300
gggtcgatta gaatccaggt ctcggcacaa ttcggctaca atcaggcagg cactgcagac    360
gtcaccaagt tccggtacat gtcttacgac cacgaccatg acatcaagga agacagtatg    420
gagaaattag ctattagtac atccggacca tgccgtcgtc ttggccacaa agggtacttc    480
ctgttagctc aatgtcctcc aggtgacagt gtaaccgtca gtatcacgag cggagcatct    540
gagaattcat gcaccgtgga gaaaaagatc aggaggaagt ttgtcggtag agaggagtac    600
ttgttcccac ctgtccatgg aaagctggta aagtgccacg tttacgatca cttgaaggag    660
acgtctgccg gatatataac tatgcacagg ccaggcccac acgcgtataa gtcctacctg    720
gaggaagcgt caggcgaagt gtacattaaa ccaccttctg gcaagaacgt cacctacgaa    780
tgtaagtgtg gtgactacag cacaggtatt gtgagcacgc gaacgaagat gaacggctgc    840
actaaagcaa aacaatgcat tgcctacaag cgcgaccaaa cgaaatgggt cttcaactcg    900
ccggatctta ttaggcacac agaccactca gtgcaaggta aactgcacat tccattccgc    960
ttgacaccga cagtctgccc ggttccgtta gctcacacgc ctacagtcac gaagtggttc   1020
aaaggcatca ccctccacct gactgcaacg cgaccaacat tgctgacaac gagaaaattg   1080
gggctgcgag cagacgcaac agcagaatgg attacgggga ctacatccag gaatttttct   1140
gtggggcgag aagggctgga gtacgtatgg ggcaaccatg aaccagtcag agtctgggcc   1200
caggagtcgg caccaggcga cccgcatgga tggccgcatg agatcatcat ccattattat   1260
catcggcatc cagtctacac tgtcattgtg ctgtgcggtg tcgctctggc tatcctggta   1320
ggcactgcat cgtcagcagc ttgtatcgcc aaagcaagaa gagactgcct gacgccatac   1380
gcgcttgcac cgaacgcaac ggtacccaca gcattagcag ttttgtgctg tattcggcca   1440
accaacgctg aaacatttgg agaaactttg aaccatctgt ggtttaacaa ccaaccgttt   1500
ctctgggcac agttgtgcat ccctctggca gcgcttatta ttctgttccg ctgcttttca   1560
tgctgcatgc ctttttttatt ggttgcaggc gtctgcctgg ggaaggtaga cgccttcgaa   1620
catgcgacca ctgtgccaaa tgttccgggg atcccgtata aggcgttggt cgaacgtgca   1680
ggttacgcgc cacttaatct ggagattacg gtcgtctcat cggaattaac accctcaact   1740
aacaaggagt acgtgacctg caaatttcac acagtcgttc cttcaccaca agttaaatgc   1800
tgcgggtccc tcgagtgtaa ggcatcctca aaagcggatt acacatgccg cgtttttggc   1860
ggtgtgtacc ctttcatgtg ggaggcgca cagtgcttct gtgacagtga gaacacacaa   1920
ctgagtgagg catacgtcga gttcgctcca gactgcacta tagatcatgc agtcgcacta   1980
aaagttcaca cagctgctct gaaagtcggc ctgcgtatag tatacggcaa taccacagcg   2040
cgcctggata cattcgtcaa cggcgtcaca ccaggttcct cacgggacct gaaggtcata   2100
gcagggccga tatcagcagc tttttcaccc tttgaccata aggtcgtcat tagaaagggg   2160
cttgtttaca actacgactt ccctgagtat ggagctatga acccaggagc gttcggcgat   2220
attcaagcat cctctcttga tgccacagac atagtagccc gcaccgacat acggctgctg   2280
```

```
aagccttctg tcaagaacat ccacgtcccc tacacccaag cagtatcagg gtatgaaatg   2340

tggaagaaca actcaggacg acccctgcaa gaaacagcac cattcggatg taaaattgaa   2400

gtggagcctc tgcgagcgac taactgtgct tatgggcaca tccctatctc gattgacatc   2460

cctgatgcag cttttgtgag atcatctgaa tcaccaacaa ttttagaagt cagctgcaca   2520

gtagcagact gcatttattc tgcagacttt ggtggttcgc taacactaca gtacaaagct   2580

aacagagagg gacattgtcc agttcactcc cactccacta cagctgtttt gaaggaagcg   2640

accacacatg tgactgccac aggcagcata acactacatt ttagcacatc gagcccacaa   2700

gcaaatttca tagtttcgct atgcggcaag aagaccacct gcaatgctga atgtaaacca   2760

ccggccgacc acataattgg agaaccacat aaggtcgacc aagaattcca ggcggcagtt   2820

tccaaaacat cttggaactg gctgcttgca ctgtttgggg gagcatcatc cctcattgtt   2880

gtaggactta tagtgttggt ctgcagctct atgcttataa acacacgtag a             2931
```

<210> SEQ ID NO 5
<211> LENGTH: 2943
<212> TYPE: DNA
<213> ORGANISM: Artificial sequence
<220> FEATURE:
<223> OTHER INFORMATION: Synthetic construct: Eastern equine encephalitis virus cassette.

<400> SEQUENCE: 5

```
tcgctcgcca ctgttatgtg cgtcctggcc aatatcacgt ttccatgtga tcaaccaccc     60

tgcatgccat gctgttatga aaagaatcca cacgaaacac tcaccatgct ggaacagaat    120

tacgacagcc gagcctatga tcagctgctc gatgccgctg tgaaatgtaa tgctaggaga    180

accaggagag atttggacac tcatttcacc cagtataagt tggcacgccc gtatattgct    240

gattgcccta actgtgggca tagtcggtgc gacagcccta tagctataga agaagtcaga    300

ggggatgcgc atgcaggagt catccgcatc cagacatcag ctatgttcgg tctgaagacg    360

gatggagtcg atttggccta catgagtttc atgaacggca aaacgcagaa atcaataaag    420

atcgacaacc tgcatgtgcg cacctcagcc ccttgttccc tcgtgtcgca ccacggctat    480

tacatcttgg ctcaatgccc accaggggac acggttacag ttgggtttca cgacgggcct    540

aaccgccata cgtgcacagt tgcccataag gtagaattca ggccagtggg tagagagaaa    600

taccgtcacc cacctgaaca tggagttgaa ctaccgtgta accgttacac tcacaagcgt    660

gcagaccaag gacactatgt tgagatgcat caaccagggc tagttgccga ccactctctc    720

cttagcatcc acagtgccaa ggtgaaaatt acggtaccga gcggcgccca agtgaaatac    780

tactgcaagt gtccagatgt acgagaggga attaccagca gcgaccatac aaccacctgc    840

acggatgtca aacaatgcag ggcttacctg attgacaaca agaaatgggt gtacaactct    900

ggaagactgc ctcgaggaga gggcgacact tttaaaggaa aacttcatgt gccctttgtg    960

cctgttaagg ccaagtgcat cgccacgctg gcaccggagc ctctagttga gcacaaacac   1020

cgcaccctga ttttacacct gcacccggac catccgacct tgctgacgac caggtcactt   1080

ggaagtgatg caaatccaac tcgacaatgg attgagcgac caacaactgt caatttcaca   1140

gtcaccggag aagggttgga gtatacctgg ggaaaccatc caccaaaaag agtatgggct   1200

caagagtcag gagaagggaa cccacatgga tggccgcacg aagtggtagt ctattactac   1260

aacagatacc cgttaaccac aattatcggg ttatgcacct gtgtggctat catcatggtc   1320

tcttgtgtca catccgtgtg gctcctttgc aggactcgca atctttgcat aaccccgtat   1380
```

-continued

```
aaactagccc cgaacgctca agtcccaata ctcctggcgt tactttgctg cattaagccg   1440

acgagggcag acgacacctt gcaagtgctg aattatctgt ggaacaacaa tcaaaacttt   1500

ttctggatgc agacgcttat cccacttgca gcgcttatcg tatgcatgcg catgctgcgc   1560

tgcttatttt gctgtgggcc ggcttttta cttgtctgcg gcgccttggg cgccgcagcg    1620

tacgaacaca cagcagtgat gccgaacaag gtggggatcc cgtataaagc tttagtcgaa   1680

cgcccaggtt atgcacccgt tcatctacag atacagctgg ttaataccag gataattcca   1740

tcaactaacc tggagtacat cacctgcaag tacaagacaa aagtgccgtc tccagtagtg   1800

aaatgctgcg gtgccactca atgtacctcc aaaccccatc ctgactatca gtgtcaggtg   1860

tttacaggtg tttacccatt catgtgggga ggagcctact gcttctgcga caccgaaaac   1920

acccagatga gcgaggcgta tgtagagcgc tcggaagagt gctctatcga ccacgcaaaa   1980

gcttataaag tacacacagg cactgttcag gcaatggtga acataactta tgggagcgtc   2040

agctggagat ctgcagatgt ctacgtcaat ggtgaaactc ccgcgaaaat aggagatgcc   2100

aaactcatca taggtccact gtcatctgcg tggtccccat tcgataacaa ggtggtggtt   2160

tatgggcatg aagtgtataa ttacgacttt cctgagtacg gcaccggcaa agcaggctct   2220

tttggagacc tgcaatcacg cacatcaacc agcaacgatc tgtacgcaaa caccaacttg   2280

aagctacaac gaccccaggc tggtatcgtg cacacacctt tcacccaggc gccctctggc   2340

ttcgaacgat ggaaaaggga caaaggggca ccgttgaacg acgtagcccc gtttggctgt   2400

tcgattgccc tggagccgct ccgtgcagaa aattgtgcag tgggaagcat ccctatatct   2460

atagatatac ccgatgcggc tttcactaga atatctgaaa caccgacagt ctcagacctg   2520

gaatgcaaaa ttacggagtg tacttatgcc tccgatttcg gtggtatagc caccgttgcc   2580

tacaaatcca gtaaagcagg aaactgtcca attcattctc catcaggtgt tgcagttatt   2640

aaagagaatg acgtcaccct tgctgagagc ggatcattta cattccactt ctccactgca   2700

aacatccatc ctgcttttaa gctgcaggtc tgcaccagtg cagttacctg caaaggagat   2760

tgcaagccac cgaaagatca tatcgtcgat tatccagcac aacataccga atcctttacg   2820

tcggcgatat ccgccaccgc gtggtcgtgg ctaaaagtgc tggtaggagg aacatcagca   2880

tttattgttc tggggcttat tgctacagca gtggttgccc tagttctgtt cttccataga   2940

cat                                                                 2943
```

TC-83-DERIVED ALPHAVIRUS VECTORS, PARTICLES AND METHODS

CROSS REFERENCE TO RELATED APPLICATIONS

This application is a continuation of U.S. patent application Ser. No. 11/132,711, filed May 18, 2005, which claims benefit of U.S. Provisional Application No. 60/572,212, filed May 18, 2004, which application is incorporated by reference herein to the extent there is no inconsistency with the present disclosure.

ACKNOWLEDGMENT OF FEDERAL RESEARCH SUPPORT

This invention was made, at least in part, through funding from the United States government, through grants from the National Institutes of Health, grant numbers 1U01 Al056438-01 and 5U01 Al 55071-02. The government has certain rights in the invention.

BACKGROUND OF THE INVENTION

The present invention relates to recombinant DNA technology, and in particular to introducing foreign nucleic acid in a eukaryotic cell, and more particularly to compositions and methods for producing alphavirus replicon particles useful in immunotherapies and/or gene therapy applications. In particular, the present invention discloses a genetic background for the alphavirus replicon particle system that is based on the Venezuelan Equine Encephalitis virus (VEE) vaccine strain, TC-83.

A variety of viruses is included in the alphavirus genus, which is a member of the Togaviridae family. The alphaviral genome is a single-stranded, messenger-sense RNA, modified at the 5'-end with a methylated cap and at the 3'-end with a variable-length poly (A) tract. Structural subunits containing a single viral protein, capsid, associate with the RNA genome in an icosahedral nucleocapsid. In the virion, the nucleocapsid is surrounded by a lipid envelope covered with a regular array of transmembrane protein spikes, each of which consists of three heterodimeric complexes of two glycoproteins, E1 and E2. See Paredes et al., (1993) *Proc. Natl. Acad. Sci. USA* 90:9095-9099. The Sindbis and Semliki Forest viruses are considered the prototypical alphaviruses and have been studied extensively. See Schlesinger, The Togaviridae and Flaviviridae, Plenum Publishing Corp., New York (1986). The VEE virus has also been studied extensively, see, e.g., U.S. Pat. Nos. 5,185,440, 5,505,947, and 5,643,736.

The use of propagation-defective alphavirus particles, termed alphaviral replicon particles, has shown great promise as a viral vector delivery system. Replicons are constructed to carry one or more heterologous antigens in place of some or all of the alphavirus structural genes. The replicons are introduced into alphavirus-permissive cells along with a helper construct(s) that expresses the viral structural protein(s) not encoded by the replicon or, alternatively, the replicon is introduced into a packaging cell capable of expressing the structural proteins. The replicon is then packaged, analogous to the packaging of the intact alphaviral genome, by the expressed structural proteins. These packaged replicons, or alphaviral replicon particles, are then inoculated into an animal. The particles enter the host cell, and the replicons then express the introduced heterologous coding or other functional sequence(s) at very high levels from the subgenomic mRNA.

Subsequent viral progeny are prevented from assembly since the replicons do not encode all of the essential viral packaging (structural) genes.

Both the alphaviral genetic background for the replicon and the alphaviral structural proteins used to package the replicon have a significant impact on the ultimate performance of the replicon particles. The VEE virus has been preferred as a vaccine vector among the alphaviruses because it is naturally lymphotrophic, which leads to strong cellular and humoral immune responses at relatively low immunization doses (Davis, N L et al. (1996) *J. Virol.* 70(6): 3781-7; MacDonald, G H and Johnston R E, (2000) *J. Virol.* 74(2): 914-922; Caley I J et al. (1997) *J. Virol.* 71: 3031-3038; Hevey M et al. (1998) *Virology* 251(1): 28-37; Caley I J et al. (1999) *Vaccine* 17:23-24; Pushko, P et al. (2001) *Vaccine* 19:142-153).

Several strains of the Venezuelan Equine Encephalitis virus (VEE) are known, and within those strains, subtypes have been recognized. Virulent VEE strains have been isolated during mosquito-borne epidemic encephalomyelitis in equids in tropical and sub-tropical areas of the New World. One of the most virulent epizootic strains, the Trinidad Donkey (TRD) strain, which is in subtype IA/B, was passaged serially in tissue culture to create a live, attenuated strain (Berge et al. (1961) *Amer. J. Hyg.* 73:209-218) known as TC-83. This strain elicits VEE-specific neutralizing antibodies in most humans and equines and has been used successfully as a vaccine in both species (McKinney et al. (1972) "Inactivated and live VEE vaccines—A Review, in Venezuelan Encephalitis, pp. 369-376, Sc. Pub. No. 243 Pan American Health Organization, Washington, D.C.; Walton T E et al. (1972) *Am. J. Epidemiol.* 95:247-254; Pittman P R et al. (1996) *Vaccine* 14(4): 337-343). Nonetheless, this vaccine presents several problems in terms of safety and efficacy. First, it can cause adverse, sometimes moderately severe reactions in human vaccines. Second, the TC-83 strain shows residual murine virulence and is lethal for suckling mice after intracerebral (i.c.) or subcutaneous (s.c.) inoculation (Ludwig G et al. (2001) *Am. J. Trop. Med. Hyg.* January-February; 64(1-2):49-55). Third, the TC-83 strain has a significant percentage of non-responders in humans, i.e., individuals who do not show a demonstrable humoral response after inoculation (Pittman P R et al. (1996) *Vaccine* 14(4): 337-343). Finally, the TC-83 strain is known to be especially sensitive to interferon, as compared to the parental TRD strain or other epizootic strains of VEE (Spotts, D R et al. (1998) *J. Virol.* 72:10286-10291). Such enhanced sensitivity to interferon would lead one to expect that the heterologous genes in a replicon particle would be expressed less efficiently in an infected cell and/or that such particles would be less immunogenic in vivo. All of these detrimental factors associated with the TC-83 vaccine strain of VEE have led previous researchers to search for better attenuated strains to use as either propagation-competent VEE vectors or in replicon particle systems (e.g. Davis N L et al. (1994) *Arch. Virol. Suppl.* 9:99-109; Davis N L et al. (1996) *J. Virol.* 70(6):3781; Pushko et al. (1997) Ibid.; Pratt W D et al. (2003) *Vaccine* 21(25-26): 3854-3862).

There is a continuing need to optimize the combination of mutations and alphavirus strain to provide the most effective alphavirus replicon particle for use in vaccine and/or gene therapy applications.

SUMMARY OF THE INVENTION

The present invention provides compositions of infective, replication-defective, highly immunogenic alphavirus replicon particles based on a particular alphavirus strain, i.e., the TC-83 of VEE, and methods of preparation thereof. As described previously (see, for example, U.S. Pat. Nos. 5,792,462; 6,156,558; 5,811,407; 6,008,035; 6,583,121; WO 03/023026; U.S. Publication No. 2003/0119182, all incorporated herein by reference), functional alphavirus replicon particles have been made from several different alphaviruses and chimeras thereof (see, for example, U.S. Publication No 2003/0148262). These particles are useful in vaccine and gene therapy applications, and the optimal characteristics of the alphavirus replicon particles differ in these applications. For instance, it may be useful to reduce the expression of proteins from the replicon during gene therapy applications, and thus techniques have been developed in the art to reduce such expression (see e.g. U.S. Pat. Nos. 5,843,723 and 6,451,592). In the case of vaccine applications, maximizing the expression of the heterologous RNA from the replicon, minimizing any anti-vector responses, and targeting the tissues and cells of the immune system are desirable features. The alphaviruses Venezuelan Equine Encephalitis (VEE) virus and South African Arbovirus No. 86 have proved particularly useful in the vaccine applications. To improve the safety of these alphavirus vectors in the rare event that a replication-competent virus is generated, at least one attenuating mutation has been introduced into the alphaviral genomic fragments. The present inventors have now discovered that the TC-83 strain of VEE can be used as the genetic background for an alphavirus replicon particle system which provides a surprisingly effective VEE particle preparation for use in immunogenic compositions and which has other surprisingly advantageous properties useful in a vaccine vector system, including the ability to prepare purified preparations with ease.

The present inventors have discovered that the TC-83 strain of VEE is a surprisingly good alphavirus strain from which to derive a replicon vaccine particle. A complete sequence of the TC-83 sequence was published (Kinney R M et al. (1989) *Virology* 170:19-30; with correction noted in Kinney R M et al. (1993) *J. Virol.* 67(3):1269-1277). The genome of this live, attenuated vaccine strain carries 12 differences from the virulent, parental strain from which it was derived. These mutations are: a single nucleotide substitution (G→A) at nucleotide 3 of the 5' non coding region; amino acid substitutions at nsP2-16 (Ala→Asp), nsP3-260 (Ser→Thr), E2-7 (Lys→Asn), E2-85 (His→Tyr), E2-120 (Thr→Arg), E2-192 (Val→Asp), E2-296 (Thr→Ile), and E1-161 (Leu→Ile); 2 silent nucleotide substitutions at E2-278 (U→C) and E1-211 (A→U), and a single nucleotide deletion at nucleotide 11,405 in the 3' non-coding region (UU→U). Kinney et al. 1993 Ibid. have suggested that the attenuated phenotype of the live TC-83 strain (i.e. reduced neurovirulence in mice) is due to the nucleotide 3 mutation (G to A) and the E2 mutations, particularly the E2-120 mutation. It has been shown that this nucleotide 3 mutation, when introduced into a wild-type strain of VEE, attenuates the strain (White L J et al. (2001) *J. Virol* 75: 3706-3718). However, the methods used do not exclude contributions from other mutations, and the existence of the numerous other nonconservative mutations in the TC-83 genome make it impossible to predict whether it can serve as an effective genetic background for the replicon particle system.

The inventors have now produced a replicon particle vaccine based on the TC-83 strain, and it has several surprisingly advantageous characteristics for both vaccine and gene therapy applications including, but not limited to, much higher yields as compared to those achieved with particles based on wild-type VEE or on those carrying other attenuating mutations; lowered anti-vector responses; increased purity; excellent immunogenicity that is comparable to other VEE strains carrying only one, two or three attenuating mutations, and no non-responsiveness, in contrast to the noted non-responsiveness of animals to the live TC-83 strain used as a vaccine.

Additionally, the inventors have discovered that packaging an alphavirus replicon in the VEETC83 structural proteins results in significantly higher yields of replicon particle vaccines from cell cultures. Thus, the VEETC83 structural proteins can be advantageously used to package replicons from other alphaviruses, including other strains of VEE.

Thus, the present invention provides a recombinant alphavirus particle comprising (i) an alphavirus replicon RNA encoding one or more heterologous RNA sequences, wherein the replicon RNA comprises a 5' sequence which initiates transcription of alphavirus RNA, one or more nucleotide sequences which together encode those TC-83 alphavirus nonstructural proteins necessary for replication of the replicon RNA, a means for expressing the polypeptide encoded by the heterologous RNA(s), and a 3' RNA polymerase recognition sequence, (ii) a TC-83 derived capsid protein; and (iii) alphavirus glycoproteins derived from TC-83.

The present invention also provides other VEE vaccine strains, especially those with characteristics similar to those of TC-83, which can be engineered for use in immunogenic replicon particle compositions.

Also provided is a population of infectious, propagation-defective, alphavirus particles, wherein the population comprises replicon particles comprising a VEE TC-83 replicon RNA comprising an alphavirus packaging signal, one or more heterologous RNA sequence(s) encoding a nucleic acid of interest and lacking sequences encoding alphavirus structural proteins, and wherein the population contains no more than 10 replication-competent TC-83 viral particles per $10^8$ TC-83 replicon particles.

Also provided is a composition comprising a population of infectious, propagation-defective, alphavirus particles, wherein (1) each particle comprises an alphavirus replicon RNA encoding one or more heterologous RNA sequences and lacks sequences encoding any alphavirus structural proteins, (2) the population has no detectable replication competent viruses (RCV), as measured by passage on cell cultures, (3) the replicon RNA is derived from TC-83, and wherein the population is formulated with a pharmaceutically acceptable carrier. The alphavirus structural proteins can be derived from the alphavirus VEE vaccine strain TC-83, a wild-type VEE strain, or other strains of VEE containing one or more attenuating mutations in the alphaviral genomic sequences encoding the structural proteins. In a specific embodiment, the TC-83 structural proteins may have one or more additional attenuating mutations introduced, e.g. at E1-81 (e.g. from Phe to Ile).

Also provided is a composition comprising a population of infectious, propagation-defective, alphavirus particles, wherein (1) each particle comprises an alphavirus replicon RNA encoding one or more heterologous RNA sequences and lacks sequences encoding any alphavirus structural proteins, (2) the structural proteins comprising the coat of the particles are derived from VEETC83, and (3) the population has no detectable replication competent viruses (RCV), as measured by passage on cell cultures, and wherein the population is formulated with a pharmaceutically acceptable carrier. In this composition, the alphavirus replicon RNA is derived from a wild-type VEE strain or other non-TC83 strains of VEE containing one or more attenuating mutations in the alphaviral genomic sequences contained within the replicon. In a specific embodiment, the TC-83 structural proteins may have one or more additional attenuating mutations introduced, e.g. at E1-81 (e.g. from Phe to Ile).

Also provided is a method of producing an immune response in a subject, comprising administering to the subject an effective amount of an immunogenic composition comprising a population of infectious, propagation-defective alphavirus particles in a pharmaceutically-acceptable carrier, wherein the composition comprises particles comprising a VEE TC-83 replicon RNA comprising an alphavirus packaging signal, one or more heterologous RNA sequence(s) encoding an immunogen and lacking sequences encoding alphavirus structural proteins, and wherein the composition has less than 10 replication-competent TC-83 particles per $10^8$ TC-83 replicon particles.

Also provided is a helper cell for producing an infectious, propagation-defective alphavirus particle comprising (1) a VEETC83 replicon RNA comprising a heterologous RNA sequence, for example, a coding sequence heterologous to the virus, and lacking sequences encoding alphavirus structural proteins; and (2) one or more nucleic acids encoding the TC-83 structural proteins. Alternatively the structural proteins can be selected from the group consisting of wild-type VEE structural glycoproteins, VEE 3014 structural glycoproteins, VEE 3040 glycoproteins, VEE 3042 glycoproteins, and VEE 3526 glycoproteins, but preferably from among VEE structural glycoproteins which contain amino acid substitutions that confer attenuated virulence, and the VEE capsid is produced from the wild-type sequence or from a sequence in which the auto-proteolytic cleavage site has been deleted.

Also provided is a helper cell for producing an infectious, propagation-defective alphavirus particle comprising (1) an alphavirus replicon RNA comprising a heterologous RNA sequence, for example, a coding sequence heterologous to the virus, and lacking sequences encoding alphavirus structural proteins; and (2) one or more nucleic acids encoding the TC-83 structural proteins.

The present invention further provides a method of producing infectious, propagation-defective TC-83 replicon particles comprising introducing into a population of cells a recombinant DNA molecule encoding all the VEE structural proteins, and a TC-83 replicon RNA encoding at least one heterologous RNA, such that infectious, propagation-defective TC-83 replicon particles are produced, and wherein the VEE structural glycoproteins are derived from one of the following VEE strains: TC-83, 3014, 3040, 3042 and 3526. These strains are referred to herein as VEETC83, VEE3014, etc.

Also provided is a method of producing infectious, propagation-defective alphavirus replicon particles comprising introducing into a population of cells a recombinant DNA molecule encoding all the VEETC83 structural proteins, and an alphavirus replicon RNA encoding at least one heterologous RNA, such that infectious, propagation-defective replicon particles are produced, and wherein the VEE replicon RNA is derived from a wild-type VEE strain or incorporates at least one attenuating mutations, such as the mutation to an A at nucleotide 3.

A method of producing infectious, propagation-defective alphavirus replicon particles comprising introducing into a population of cells (i) two recombinant nucleic acid molecules, each of which encodes at least one, but not all of VEE structural proteins and (ii) a TC-83 replicon RNA encoding at least one heterologous RNA, wherein the two recombinant nucleic acid molecules together encode all VEE structural proteins required to produce infectious, propagation-defective TC-83 replicon particles in the cells, and further wherein the alphaviral structural proteins are derived from one of the following VEE strains: TC-83, 3014, 3040, 3042 and 3526. These strains are typically referred to in this application as "VEETC83", "VEE3014," etc.

Also provided is a method of providing advantageously purified, infectious, propagation-defective TC-83 replicon particles by heparin affinity chromatography, either by column or batch purification methods. The unique heparin-binding characteristics of the TC-83 derived replicon particles allow for removal of contaminating proteins and nucleic acids through a single purification step.

Also provided are methods of eliciting an immune response in a subject, comprising administering to the subject an immunogenic amount of the population of replicon particles of this invention.

The present invention is also applicable to the production of live attenuated alphavirus vaccines, which may or may not carry heterologous genes for expression in the vaccinee, as described in U.S. Pat. No. 5,643,576, or live attenuated alphavirus vectors which direct the expression of functional RNAs (such as antisense, suppressing RNAs or interfering RNAs or RNAs which encode therapeutic proteins. The method of the present invention comprises the steps of (a) introducing the TC-83 replicon nucleic acid into a host cell, wherein said replicon nucleic acid contains at least an alphavirus packaging signal and at least one coding sequence for a protein or functional RNA of interest expressible in said alphaviral replicon nucleic acid, wherein the host cell is capable of expressing alphavirus structural proteins required to produce ARPs, to produce a modified host cell; (b) culturing said modified host cell in a medium under conditions allowing expression of the structural proteins and replication of the alphaviral replicon nucleic acid, and then packaging of the alphaviral replicon nucleic acid to form ARPs; (c), optionally separating the modified host cells from the medium, and (d) after step (b) or (c) contacting the modified host cells with an aqueous solution having an ionic strength of at least approximately 0.20 M, desirably from about 0.5 to about 5 M, (herein the "Release Medium") to release the ARPs into the aqueous solution to produce an ARP-containing solution. The ionic strength of the Release Medium can be achieved using salts which do not inactivate the virions or ARPs, and suitable salts include, but are not limited to, sodium chloride, magnesium chloride, ammonium chloride, ammonium acetate, potassium chloride, calcium chloride, ammonium bicarbonate, and heparin Fast Flow. Desirably the Release Medium comprises a buffer with a pH from about 6 to about 9, preferably from about 6.5 to about 8.5. Where the cells are not separated from the medium, the ionic strength of the medium can be raised by the addition of solid salts or a concentrated solution to provide the increased ionic strength for releasing the ARPs (or virions) from the cells.

DETAILED DESCRIPTION OF THE INVENTION

Figure 1:
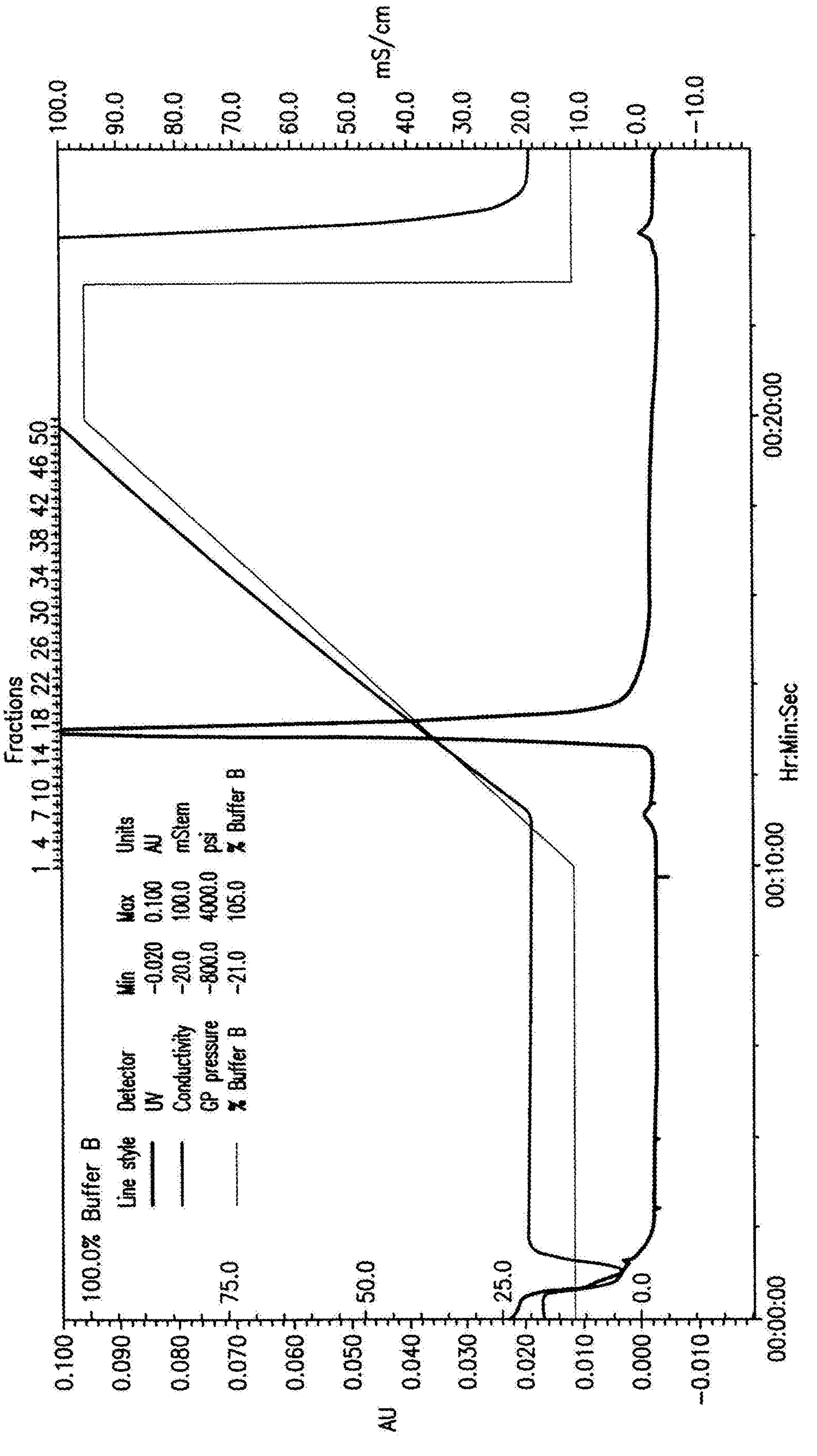
FIG. 1 shows the elution profile of TC-83 virus replicon particles during heparin affinity chromatography.

The following discussion and definitions are provided to improve the clarity of the present disclosure to one of ordinary skill in the relevant art.

In the context of the present application, nm means nanometer, ml means milliliter, VEE means Venezuelan Equine Encephalitis virus, EMC means Encephalomyocarditis virus, BHK means baby hamster kidney cells, HA means hemagglutinin gene, GFP means green fluorescent protein gene, N means nucleocapsid, FACS means fluorescence activated cell sorter, IRES means internal ribosome entry site, and FBS means Fetal Bovine Serum. The expression "E2 amino acid (e.g., Lys, Thr, etc.) number" indicates designated amino acid at the designated residue of the E2 gene, and is also used to refer to amino acids at specific residues in the E1 gene.

As used herein, the term "alphavirus" has its conventional meaning in the art, and includes the various species such as VEE, SFV, Sindbis, Ross River Virus, Western Equine Encephalitis Virus, Eastern Equine Encephalitis Virus, Chikungunya, S.A. AR86, Everglades virus, Mucambo, Barmah Forest Virus, Middelburg Virus, Pixuna Virus, O'nyong-nyong Virus, Getah Virus, Sagiyama Virus, Bebaru Virus, Mayaro Virus, Una Virus, Aura Virus, Whataroa Virus, Banbanki Virus, Kyzylagach Virus, Highlands J Virus, Fort Morgan Virus, Ndumu Virus, and Buggy Creek Virus. The preferred alphaviruses used in the constructs and methods of the claimed invention are VEE, S.A. AR86, Sindbis (e.g. TR339, see U.S. Pat. No. 6,008,035), and SFV.

"Alphavirus-permissive cells" employed in the methods of the present invention are cells that, upon transfection with a complete viral RNA transcript, are capable of producing viral particles. Alphaviruses have a broad host range. Examples of suitable packaging cells include, but are not limited to, Vero cells, baby hamster kidney (BHK) cells, chicken embryo fibroblast cells, DF-1, 293, 293T, Chinese Hamster Ovary (CHO) cells, and insect cells.

As used herein, the phrases "attenuating mutation" and "attenuating amino acid," mean a nucleotide mutation (which may or may not be in a region of the viral genome encoding polypeptides) or an amino acid coded for by a nucleotide mutation, which in the context of a live virus, result in a decreased probability of the alphavirus causing disease in its host (i.e., a loss of virulence), in accordance with standard terminology in the art, See, e.g., B. Davis, et al., *Microbiology* 132 (3*d* ed. 1980), whether the mutation be a substitution mutation, or an in-frame deletion or addition mutation. The phrase "attenuating mutation" excludes mutations which would be lethal to the virus, unless such a mutation is used in combination with a "restoring" mutation which renders the virus viable, albeit attenuated. Exemplary attenuating mutations in VEE structural proteins include, but are not limited to, those described in U.S. Pat. No. 5,505,947 to Johnston et al., U.S. Pat. No. 5,185,440 to Johnston et al., U.S. Pat. No. 5,643,576 to Davis et al., U.S. Pat. No. 5,792,462 to Johnston et al., and U.S. Pat. No. 5,639,650 to Johnston et al., the disclosures of which are incorporated herein in their entireties by reference. Specific attenuating mutations for the VEE E1 glycoprotein include an attenuating mutation at any one of amino acid positions 81, 272 or 253. Alphavirus replicon particles made from the VEE-3042mutant contain an isoleucine substitution at E1-81, (amino acid 81 of the E1 protein) and virus replicon particles made from the VEE-3040 mutant contain an attenuating mutation at E1-253. Specific attenuating mutations for the VEE E2 glycoprotein include an attenuating mutation at any one of amino acid positions 76, 120 , or 209. Alphavirus replicon particles made from the VEE-3014 mutant contain attenuating mutations at both E1-272 and at E2-209 (see U.S. Pat. No. 5,792,462). A specific attenuating mutation for the VEE E3 glycoprotein includes an attenuating mutation consisting of a deletion of amino acids 56-59. Virus replicon particles made from the VEE-3526 mutant contain this deletion in E3 (aa56-59) as well as a second attenuating mutation at E1-253. For alphaviruses generally, deletion or substitution mutations in the cleavage domain between E3 and E2, which result in the E3/E2 polyprotein not being cleaved, are attenuating.

The terms "5' alphavirus replication recognition sequence" and "3' alphavirus replication recognition sequence" refer to the sequences found in alphaviruses, or sequences derived therefrom, that are recognized by the nonstructural alphavirus replicase proteins and lead to replication of viral RNA. These are sometimes referred to as the 5' and 3' ends, or alphavirus 5' and 3' sequences. In the constructs of this invention, the use of these 5' and 3' ends will result in replication of the RNA sequence encoded between the two ends. The 3' alphavirus replication recognition sequence as found in the alphavirus is typically approximately 300 nucleotides in length, which contains a more well defined, minimal 3' replication recognition sequence. The minimal 3' replication recognition sequence, conserved among alphaviruses, is a 19 nucleotide sequence (Hill et al., *J. Virology,* 2693-2704, 1997). These sequences can be modified by standard molecular biological techniques to further minimize the potential for recombination or to introduce cloning sites, with the proviso that they must be recognized by the alphavirus replication machinery.

The term "minimal 5' alphavirus replication recognition sequence" refers to the minimal sequence that allows recognition by the nonstructural proteins of the alphavirus but does not result in significant packaging/recombination of RNA molecules containing the sequence. In a preferred embodiment, the minimal 5' alphavirus replication recognition sequence results in a fifty to one-hundred fold decrease in the observed frequency of packaging/recombination of the RNA containing that sequence. Packaging/recombination of helpers can be assessed by several methods, e.g. the method described by Lu and Silver (*J. Virol. Methods* 2001, 91(1): 59-65).

The terms "alphavirus RNA replicon", "alphavirus replicon RNA", "alphavirus RNA vector replicon", "replicon", and "vector replicon RNA" are used interchangeably to refer to an RNA molecule expressing nonstructural protein genes such that it can direct its own replication (amplification) and comprises, at a minimum, 5' and 3' alphavirus replication recognition sequences (which may be the minimal sequences, as defined above, but may alternatively be the entire regions from the alphavirus), coding sequences for alphavirus nonstructural proteins, and a polyadenylation tract. It may additionally contain a promoter and/or an IRES. Specific replicons useful in the claimed invention include: a replicon based on VEETC83, herein referred to as a "VEETC83 replicon"; a replicon based on the wild-type sequence of VEE, herein referred to as a "VEE3000 replicon"; and a replicon based on VEE3000 but additionally including one of the attenuating mutations present in TC83, namely the mutation to an "A" at nucleotide 3, herein referred to as "VEE3000nt3A".

The alphavirus RNA vector replicon is designed to express a heterologous nucleic acid, e.g. a gene, of interest, also referred to herein as a heterologous RNA or heterologous sequence, which can be chosen from a wide variety of sequences derived from viruses, prokaryotes or eukaryotes. Examples of categories of heterologous sequences include, but are not limited to, immunogens, including antigenic proteins, cytokines, toxins, therapeutic proteins, enzymes, antisense sequences, and immune response modulators.

The alphavirus RNA replicons of this invention may also be engineered to express alphavirus structural proteins, thereby generating a vaccine against the alphavirus(es) from which the structural proteins are derived. Johnston et al. and Polo et al. (cited in the background) describe numerous constructs for such alphavirus RNA replicons, and such constructs are incorporated herein by reference. Specific embodiments of the alphavirus RNA replicons utilized in the claimed invention may contain one or more attenuating mutations, an attenuating mutation being a nucleotide deletion, addition, or substitution of one or more nucleotide(s), or a mutation that comprises rearrangement or chimeric construction which results in a loss of virulence in a live virus containing the mutation as compared to the appropriate wild-type alphavirus. Examples of an attenuating nucleotide substitution (resulting in an amino acid change in the replicon) include a mutation at nsP1 amino acid position 538, nsP2 amino acid position 96, or nsP2 amino acid position 372 in the alphavirus S.A.AR86.

The terms "alphavirus structural protein/protein(s)" refers to one or a combination of the structural proteins encoded by alphaviruses. These are produced by the virus as a polyprotein and are represented generally in the literature as C-E3-E2-6k-E1. E3 and 6k serve as membrane translocation/transport signals for the two glycoproteins, E2 and E1. Thus, use of the term E1 herein can refer to E1, E3-E1, 6k-E1, or E3-6k-E1, and use of the term E2 herein can refer to E2, E3-E2, 6k-E2, or E3-6k-E2.

The term "helper(s)" or helper constructs refers to a nucleic acid molecule that is capable of expressing one or more alphavirus structural proteins.

The terms "helper cell" and "packaging cell" are used interchangeably herein and refer to the cell in which alphavirus replicon particles are produced. The helper cell comprises a set of helpers that encode one or more alphavirus structural proteins. As disclosed herein, the helpers may be RNA or DNA. The cell can be any cell that is alphavirus-permissive. In certain embodiments of the claimed invention, the helper or packaging cell may additionally include a heterologous RNA-dependent RNA polymerase and/or a sequence-specific protease.

The terms "alphavirus replicon particles", "virus replicon particles", "VRPs" or "recombinant alphavirus particles", used interchangeably herein, mean a virion-like structural complex incorporating an alphavirus replicon RNA that expresses one or more heterologous RNA sequences. Typically, the virion-like structural complex includes one or more alphavirus structural proteins embedded in a lipid envelope enclosing a nucleocapsid comprised of capsid and replicon RNA. The lipid envelope is typically derived from the plasma membrane of the cell in which the particles are produced. Preferably, the alphavirus replicon RNA is surrounded by a nucleocapsid structure comprised of the alphavirus capsid protein, and the alphavirus glycoproteins are embedded in the cell-derived lipid envelope. These replicon particles are propagation-defective (or synonymously "replication defective"), which means that the particles produced in a given host cell cannot produce progeny particles in the host cell, due to the absence of the helper function, i.e. the alphavirus structural proteins required for packaging the replicon nucleic acid. However, the replicon nucleic acid is capable of replicating itself and being expressed within the host cell into which it has been introduced. Replicon particles of this invention may be referred to as VEETC83 replicon particles, and this refers to particles comprising either a TC83 replicon RNA or TC83 structural proteins, or both a TC83 replicon RNA and TC83 structural proteins.

Any amino acids which occur in the amino acid sequences referred to in the specification have their usual three- and one-letter abbreviations routinely used in the art: A, Ala, Alanine; C, Cys, Cysteine; D, Asp, Aspartic Acid; E, Glu, Glutamic Acid; F, Phe, Phenylalanine; G, Gly, Glycine; H, H is, Histidine; I, Ile, Isoleucine; K, Lys, Lysine; L, Leu, Leucine; M, Met, Methionine; N, Asn, Asparagine; P, Pro, Proline; Q, Gln, Glutamine; R, Arg, Arginine; S, Ser, Serine; T, Thr, Threonine; V, Val, Valine; W, Try, Tryptophan; Y, Tyr, Tyrosine.

As used herein, expression directed by a particular sequence is the transcription of an associated downstream sequence, i.e. production of messenger RNA from a DNA molecule or production of messenger RNA from an alphavirus subgenomic promoter. If appropriate and desired for the particular application, the transcribed mRNA is then translated, i.e. protein is synthesized. Thus, in one embodiment of this invention, the replicon or helper construct comprises a subgenomic promoter which directs transcription of a messenger RNA encoding the heterologous nucleic acid of interest (NOI) or the transcription of an mRNA encoding one or more alphavirus structural proteins, respectively. These mRNAs are "capped" within the eukaryotic cell, i.e. a methyl-7-guanosine (5')pppN structure is present at the 5' end of the mRNA (the "cap" or "5' cap"), and this cap is recognized by the translation initiation factors that synthesize protein from the mRNA. Thus, the 26S promoter directs transcription, and the "cap" provides the initiation signal for translation.

In another embodiment, the replicon or helper construct comprises a promoter that directs transcription; an IRES element; and a coding sequence, and the IRES element is operably located such that translation of the coding sequence is via a cap-independent mechanism directed by the IRES element, either in whole or in part, described in detail in WIPO Publication No. WO 2004/085660. In particular, control of nucleic acid expression at the level of translation is accomplished by introducing an internal ribosome entry site (IRES) downstream of an alphavirus 26S subgenomic promoter and upstream of the coding sequence to be translated. The IRES element is positioned so that it directs translation of the mRNA, thereby minimizing, limiting or preventing initiation of translation of the mRNA from the 5' cap. This "IRES-directed," cap-independent translation does not require or result in any significant modification of alphavirus non-structural protein genes that could alter replication and transcription. In specific embodiments, the replicon and/or helper construct can comprise a spacer nucleic acid located between the promoter and the IRES element. The spacer nucleic acid can comprise or consist of any random or specific non-coding nucleic acid sequence which is of a length sufficient to prevent at least some, and in some embodiments, all translation from the 5' cap of a messenger RNA, such that translation is then directed by the IRES, in part or in whole. Alternatively, the spacer nucleic acid can be of a length and sequence structure that imparts sufficient secondary structure to the nucleic acid to prevent at least some and possibly all translation activity from the 5' cap of a messenger RNA.

Suitable IRES elements include, but are not limited to, viral IRES elements from picornaviruses, e.g., poliovirus (PV) or the human enterovirus 71, e.g. strains 7423/MS/87 and BrCr thereof; from encephalomyocarditis virus (EMCV); from foot-and-mouth disease virus (FMDV); from flaviviruses, e.g., hepatitis C virus (HCV); from pestiviruses, e.g., classical swine fever virus (CSFV); from retroviruses, e.g., murine leukemia virus (MLV); from lentiviruses, e.g., simian immunodeficiency virus (SIV); from cellular mRNA IRES elements such as those from translation initiation factors, e.g., eIF4G or DAP5; from transcription factors, e.g., c-Myc (Yang and Sarnow, *Nucleic Acids Research* 25: 2800-2807 (1997)) or NF-κB-repressing factor (NRF); from growth factors, e.g., vascular endothelial growth factor (VEGF), fibroblast growth factor (FGF-2) and platelet-derived growth factor B (PDGF B); from homeotic genes, e.g., *Antennapedia*; from survival proteins, e.g., X-linked inhibitor of apoptosis (XIAP) or Apaf-1; from chaperones, e.g., immunoglobulin heavy-chain binding protein BiP (Martinez-Salas et al., *Journal of General Virology* 82: 973-984, (2001)), from plant viruses, as well as any other IRES elements now known or later identified.

In specific embodiments, the IRES element of this invention can be derived from, for example, encephalomyocarditis virus (EMCV, GenBank accession # NC001479), cricket paralysis virus (GenBank accession # AF218039), *Drosophila* C virus (GenBank accession # AF014388), *Plautia stali* intestine virus (GenBank accession # AB006531), *Rhopalosiphum padi* virus (GenBank accession # AF022937), Himetobi P virus (GenBank accession # AB017037), acute bee paralysis virus (GenBank accession # AF150629), Black queen cell virus (GenBank accession #AF183905), Triatoma virus (GenBank accession # AF178440), *Acyrthosiphon pisum* virus (GenBank accession # AF024514), infectious flacherie virus (GenBank accession # AB000906), and/or Sacbrood virus (Genbank accession # AF092924). In addition, synthetic IRES elements have been described, which can be designed, according to methods know in the art to mimic the function of naturally occurring IRES elements (see Chappell, S A et al. Proc. Natl. Acad. Sci. USA (2000) 97(4):1536-41.

In specific embodiments, the IRES element can be an insect IRES element or other non-mammalian IRES element that is functional in the particular helper cell line chosen for packaging of the recombinant alphavirus particles of this invention, but would not be functional, or would be minimally functional, in a target host cell for the particles (e.g. a human subject). This is useful for those NOIs which are either toxic to the packaging cell or are detrimental to the alphavirus packaging process.

The phrases "structural protein" or "alphavirus structural protein" as used herein refer to one or more of the alphaviral-encoded proteins which are required for packaging of the RNA replicon, and typically include the capsid protein, E1 glycoprotein, and E2 glycoprotein in the mature alphavirus (certain alphaviruses, such as Semliki Forest Virus, contain an additional protein, E3, in the mature coat). The term "alphavirus structural protein(s)" refers to one or a combination of the structural proteins encoded by alphaviruses. These are synthesized (from the viral genome) as a polyprotein and are represented generally in the literature as C-E3-E2-6k-E1. E3 and 6k serve as membrane translocation/transport signals for the two glycoproteins, E2 and E1. Thus, use of the term E1 herein can refer to E1, E3-E1, 6k-E1, or E3-6k-E1, and use of the term E2 herein can refer to E2, E3-E2, 6k-E2, or E3-6k-E2.

As described herein, the nucleic acid sequences encoding structural proteins of the alphavirus are distributed among one or more helper nucleic acid molecules (e.g., a first helper RNA (or DNA) and a second helper RNA (or DNA)). In addition, one or more structural proteins may be located on the same molecule as the replicon nucleic acid, provided that at least one structural protein is deleted from the replicon RNA such that the replicon and resulting alphavirus particle are propagation defective with respect to the production of further alphavirus particles. As used herein, the terms "deleted" or "deletion" mean either total deletion of the specified segment or the deletion of a sufficient portion of the specified segment to render the segment inoperative or nonfunctional, in accordance with standard usage. See, e.g., U.S. Pat. No. 4,650,764 to Temin et al. Distribution of the helper nucleic acid sequences among multiple nucleic acid molecules minimizes the frequency at which replication competent virus (RCV) are generated through recombination events. In the case of the DNA helper constructs that do not employ alphaviral recognition signals for replication and transcription, the theoretical frequency of recombination is lower than the bipartite RNA helper systems that employ such signals.

The helper cell, also referred to as a packaging cell, used to produce the infectious, propagation defective alphavirus particles, must express or be capable of expressing alphavirus structural proteins sufficient to package the replicon nucleic acid. The structural proteins can be produced from a set of RNAs, typically two, that are introduced into the helper cell concomitantly with or prior to introduction of the replicon vector. The first helper RNA includes RNA encoding at least one alphavirus structural protein but does not encode all alphavirus structural proteins. The first helper RNA may comprise RNA encoding the alphavirus E1 glycoprotein, but not encoding the alphavirus capsid protein and the alphavirus E2 glycoprotein. Alternatively, the first helper RNA may comprise RNA encoding the alphavirus E2 glycoprotein, but not encoding the alphavirus capsid protein and the alphavirus E1 glycoprotein. In a further embodiment, the first helper RNA may comprise RNA encoding the alphavirus E1 glycoprotein and the alphavirus E2 glycoprotein, but not the alphavirus capsid protein. In a fourth embodiment, the first helper RNA may comprise RNA encoding the alphavirus capsid, but none of the alphavirus glycoproteins. In a fifth embodiment, the first helper RNA may comprise RNA encoding the capsid and one of the glycoproteins, i.e. either E1 or E2, but not both.

In preferred embodiments employing two helper RNAs, in combination with any one of these first helper RNAs, the second helper RNA encodes the one or more alphavirus structural proteins not encoded by the first helper RNA. For example, where the first helper RNA encodes only the alphavirus E1 glycoprotein, the second helper RNA encodes both the alphavirus capsid protein and the alphavirus E2 glycoprotein. Where the first helper RNA encodes only the alphavirus capsid protein, the second helper RNA encodes both the alphavirus glycoproteins. Where the first helper RNA encodes only the alphavirus E2 glycoprotein, the second helper RNA encodes both the alphavirus capsid protein and the alphavirus E1 glycoprotein. Where the first helper RNA encodes both the capsid and alphavirus E1 glycoprotein, the second helper RNA may include RNA encoding one or both of the alphavirus capsid protein and the alphavirus E2 glycoprotein.

In all of the helper nucleic acids, it is understood that these molecules further comprise sequences necessary for expression (encompassing translation and where appropriate, transcription or replication signals) of the encoded structural protein sequences in the helper cells. Such sequences can include, for example, promoters (either viral, prokaryotic or eukaryotic, inducible or constitutive), IRESes, and 5' and 3' viral replicase recognition sequences. In the case of the helper nucleic acids expressing one or more glycoproteins, it is understood from the art that these sequences are advantageously expressed with a leader or signal sequence at the N-terminus of the structural protein coding region in the nucleic acid constructs. The leader or signal sequence can be derived from the alphavirus, for example E3 or 6k, or it can be a heterologous sequence such as a tissue plasminogen activator signal peptide or a synthetic sequence. Thus, as an example, a first helper nucleic acid may be an RNA molecule encoding capsid-E3-E1, and the second helper nucleic acid may be an RNA molecule encoding capsid-E3-E2. Alternatively, the first helper RNA can encode capsid alone, and the second helper RNA can encode E3-E2-6k-E1. Additionally, the packaging signal(s) or "encapsidation sequence(s)" that are present in the viral genome are not present in all of the helper nucleic acids. Preferably, any such packaging signal(s) are deleted from all of the helper nucleic acids.

Production of Alphavirus Particles

Alphavirus replicon particles of this invention are produced by introducing helper constructs and replicon nucleic acids into a helper cell so that the helper and replicon molecules function to produce alphavirus replicon particles. In embodiments utilizing RNA helpers, the helpers can be introduced into the cells in a number of ways. The RNAs can be introduced as RNA or DNA molecules that can be expressed in the helper cell without integrating into the cell genome. Methods of introduction include electroporation, viral vectors (e.g. SV40, adenovirus, nodavirus, astrovirus), and lipid-mediated transfection. Alternatively, they can be expressed from one or more expression cassettes that have been stably transformed into the cells, thereby establishing packaging cell lines (see, for example, U.S. Pat. No. 6,242,259).

In other embodiments, the helper is a single DNA molecule which encodes all the polypeptides necessary for packaging the viral replicon RNA into infective alphavirus replicon particles. The single DNA helper can be introduced into the packaging cell by any means known to the art, including by electroporation, typically with an increase in voltage as compared to that required for the uptake of RNA, but a voltage not sufficiently high to destroy the ability of the packaging cells to produce infectious alphavirus replicon particles. The DNA helper can be introduced prior to, concomitantly, with, or after introduction/expression of the alphavirus RNA vector replicon. Alternatively, the helper function, in this format and under an inducible promoter, can be incorporated into the packaging cell genome prior to the introduction/expression of the alphavirus RNA vector replicon, and then induced with the appropriate stimulus just prior to, concomitant with, or after the introduction of the alphavirus RNA vector replicon.

Recombinant DNA molecules that express the alphavirus structural proteins can also be generated from a single helper that resolves itself into two separate molecules in vivo. Thus, the advantage of using a single helper in terms of ease of manufacturing and efficiency of production is preserved, while the advantages of a bipartite helper system are captured in the absence of employing a bipartite expression system. A DNA helper construct can be used, while in a second set an RNA helper vector is used. Such systems are described in detail in Smith et al. "Alphavirus Replicon Vector Systems", U.S. Patent Publication 2003-0119182A1, incorporated herein by reference.

For the DNA helper constructs, a promoter for directing transcription of RNA from DNA, i.e. a DNA dependent RNA polymerase, is employed. In the present context, a promoter is a sequence of nucleotides recognized by a polymerase and sufficient to cause transcription of an associated (downstream) sequence. In some embodiments of the claimed invention, the promoter is constitutive (see below). Alternatively, the promoter may be regulated, i.e., not constitutively acting to cause transcription of the associated sequence. If inducible, there are sequences present which mediate regulation of expression so that the associated sequence is transcribed only when (i) an inducer molecule is present in the medium in or on which the cells are cultivated, or (ii) conditions to which the cells are exposed are changed to be inducing conditions. In the present context, a transcription regulatory sequence includes a promoter sequence and can further include cis-active sequences for regulated expression of an associated sequence in response to environmental signals.

In the RNA helper embodiments, the promoter is utilized to synthesize RNA in an in vitro transcription reaction, and specific promoters suitable for this use include the SP6, T7, and T3 RNA polymerase promoters. In the DNA helper embodiments, the promoter functions within a cell to direct transcription of RNA. Potential promoters for in vivo transcription of the construct include eukaryotic promoters such as RNA polymerase II promoters, RNA polymerase III promoters, or viral promoters such as MMTV and MoSV LTR, SV40 early region, RSV or CMV. Many other suitable mammalian and viral promoters for the present invention are available in the art. Alternatively, DNA dependent RNA polymerase promoters from bacteria or bacteriophage, e.g. SP6, T7, and T3, may be employed for use in vivo, with the matching RNA polymerase being provided to the cell, either via a separate plasmid, RNA vector, or viral vector. In a specific embodiment, the matching RNA polymerase can be stably transformed into a helper cell line under the control of an inducible promoter.

DNA constructs that function within a cell can function as autonomous plasmids transfected into the cell or they can be stably transformed into the genome. In these embodiments, the promoter may be a constitutive promoter, i.e. a promoter which, when introduced into a cell and operably linked to a downstream sequence, directs transcription of the downstream sequence upon introduction into the cell, without the need for the addition of inducer molecules or a change to inducing conditions. Alternatively, the promoter may be inducible, so that the cell will only produce the functional messenger RNA encoded by the construct when the cell is exposed to the appropriate stimulus (inducer). When using an inducible promoter, the helper constructs are introduced into the packaging cell concomitantly with, prior to, or after exposure to the inducer, and expression of the alphavirus structural proteins occurs when both the constructs and the inducer are present. Alternatively, constructs designed to function within a cell can be introduced into the cell via a viral vector, e.g. adenovirus, poxvirus, adeno-associated virus, SV40, retrovirus, nodavirus, picornavirus, vesicular stomatitis virus, and baculoviruses with mammalian pol II promoters.

Once an RNA transcript (mRNA) encoding the helper or alphavirus RNA replicon vectors of this invention is present in the helper cell (either via in vitro or in vivo approaches, as described above), it is eventually translated to produce the encoded polypeptides or proteins. In certain embodiments, the alphavirus RNA vector replicon is transcribed in vitro from a DNA plasmid and then introduced into the helper cell by electroporation. In other embodiments, the RNA vector replicon of this invention is transcribed in vivo from a DNA vector plasmid that is transfected into the helper cell (e.g. see U.S. Pat. No. 5,814,482), or it is delivered to the helper cell via a virus or virus-like particle.

In the embodiments of this invention, one or more of the nucleic acids encoding the alphavirus RNA replicon or helpers is comprised of sequences derived from the VEETC83 genome, which contains mutations that contribute to the attenuated nature of the TC83 vaccine strain, as described hereinabove. In addition, one or more of the nucleic acids encoding the alphavirus structural proteins, i.e., the capsid, E1 glycoprotein and E2 glycoprotein, or the replicon construct, may contain one or more additional attenuating mutations.

Methods for Immunizing Subjects

As used herein, "eliciting an immune response" and "immunizing a subject" includes the development, in a subject, of a humoral and/or a cellular immune response to a protein and/or polypeptide produced by the particles and/or compositions of this invention (e.g. an immunogen, an antigen, an immunogenic peptide, and/or one or more epitopes). A "humoral" immune response, as this term is well known in the art, refers to an immune response comprising antibodies, while a "cellular" immune response, as this term is well known in the art, refers to an immune response comprising T-lymphocytes and other white blood cells, especially the immunogen-specific response by HLA-restricted cytolytic T-cells, i.e., "CTLs." A cellular immune response occurs when the processed immunogens, i.e., peptide fragments, are displayed in conjunction with the major histocompatibility complex (MHC) HLA proteins, which are of two general types, class I and class II. Class I HLA-restricted CTLs generally bind 9-mer peptides and present those peptides on the cell surface. These peptide fragments in the context of the HLA Class I molecule are recognized by specific T-Cell Receptor (TCR) proteins on T-lymphocytes, resulting in the activation of the T-cell. The activation can result in a number of functional outcomes including, but not limited to, expansion of the specific T-cell subset resulting in destruction of the cell bearing the HLA-peptide complex directly through cytotoxic or apoptotic events or the activation of non-destructive mechanisms, e.g., the production of interferon/cytokines. Presentation of immunogens via Class I MHC proteins typically stimulates a CD8+CTL response.

Another aspect of the cellular immune response involves the HLA Class II-restricted T-cell responses, involving the activation of helper T-cells, which stimulate and focus the activity of nonspecific effector cells against cells displaying the peptide fragments in association with the MHC molecules on their surface. At least two types of helper cells are recognized: T-helper 1 cells (Th1), which secrete the cytokines interleukin 2 (IL-2) and interferon-gamma and T-helper 2 cells (Th2), which secrete the cytokines interleukin 4 (IL-4), interleukin 5 (IL-5), interleukin 6 (IL-6) and interleukin 10 (IL-10). Presentation of immunogens via Class II MHC proteins typically elicits a CD4+CTL response as well as stimulation of B lymphocytes, which leads to an antibody response.

An "immunogenic polypeptide," "immunogenic peptide," or "immunogen" as used herein includes any peptide, protein or polypeptide that elicits an immune response in a subject and in certain embodiments, the immunogenic polypeptide is suitable for providing some degree of protection to a subject against a disease. These terms can be used interchangeably with the term "antigen."

In certain embodiments, the immunogen of this invention can comprise, consist essentially of or consist of one or more "epitopes." An "epitope" is a set of amino acid residues which is involved in recognition by a particular immunoglobulin. In the context of T cells, an epitope is defined as the amino acid residues necessary for recognition by T cell receptor proteins and/or MHC receptors. In an immune system setting, in vivo or in vitro, an epitope refers to the collective features of a molecule, such as primary, secondary and/or tertiary peptide structure, and/or charge, that together form a site recognized by an immunoglobulin, T cell receptor and/or HLA molecule. In the case of a B-cell (antibody) epitope, it is typically a minimum of 3-4 amino acids, preferably at least 5, ranging up to approximately 50 amino acids. Preferably, the humoral response-inducing epitopes are between 5 and 30 amino acids, usually between 12 and 25 amino acids, and most commonly between 15 and 20 amino acids. In the case of a T-cell epitope, an epitope includes at least about 7-9 amino acids, and for a helper T-cell epitope, at least about 12-20 amino acids. Typically, such a T-cell epitope will include between about 7 and 15 amino acids, e.g., 7, 8, 9, 10, 11, 12, 13, 14 or 15 amino acids.

The alphavirus particles of this invention are employed to express a nucleic acid encoding an immunogenic polypeptide in a subject (e.g., for vaccination) or for immunotherapy (e.g., to treat a subject with cancer or tumors). Thus, in the case of vaccines, the present invention thereby provides methods of eliciting an immune response in a subject, comprising administering to the subject an immunogenic amount of a population of alphavirus particles.

An "immunogenic amount" is an amount of the infectious alphavirus particles which is sufficient to evoke an immune response in the subject to which the pharmaceutical formulation comprising the alphavirus particles is administered. An amount of from about $10^4$ to about $10^9$, especially $10^6$ to $10^8$, infectious units, per dose is believed suitable, depending upon the age and species of the subject being treated. Exemplary pharmaceutically acceptable carriers include, but are not limited to, sterile pyrogen-free water and sterile pyrogen-free physiological saline solution.

A "subject" of this invention includes, but is not limited to, warm-blooded animals, e.g., humans, non-human primates, horses, cows, cats, dogs, pigs, rats, and mice. Administration of the various compositions of this invention (e.g., nucleic acids, particles, populations, pharmaceutical compositions) can be accomplished by any of several different routes. In specific embodiments, the compositions can be administered intramuscularly, subcutaneously, intraperitoneally, intradermally, intranasally, intracranially, sublingually, intravaginally, intrarectally, orally, or topically. The compositions herein may be administered via a skin scarification method, or transdermally via a patch or liquid. The compositions may be delivered subdermally in the form of a biodegradable material which releases the compositions over a period of time.

The compositions of this invention can be used prophylactically to prevent disease or therapeutically to treat disease. Diseases that can be treated include infectious disease caused by viruses, bacteria, fungi or parasites, and cancer. Chronic diseases involving the expression of aberrant or abnormal proteins or the over-expression of normal proteins, can also be treated, e.g., Alzheimer's, disease multiple sclerosis, stroke, etc.

The compositions of this invention can be optimized and combined with other vaccination regimens to provide the broadest (i.e., all aspects of the immune response, including those features described hereinabove) cellular and humoral responses possible. In certain embodiments, this can include the use of heterologous prime-boost strategies, in which the compositions of this invention are used in combination with a composition comprising a different modality for vaccination, such as one or more of the following: immunogens derived from a pathogen or tumor, recombinant immunogens, naked nucleic acids, nucleic acids formulated with lipid-containing moieties, non-alphavirus vectors (including but not limited to pox vectors, adenoviral vectors, herpes vectors, vesicular stomatitis virus vectors, paramyxoviral vectors, parvovirus vectors, papovavirus vectors, retroviral vectors), and other alphavirus vectors. The viral vectors can be virus-like particles or nucleic acids. The alphavirus vectors can be replicon-containing particles, DNA-based replicon-containing vectors (sometimes referred to as an "ELVIS" system, see, for example, U.S. Pat. No. 5,814,482) or naked RNA vectors. In specific embodiments, VRPs can be used as a priming inoculation, followed by one or more boosting inoculations using one of the above-listed compositions. Alternatively, VRPs can be used in one or more boosting inoculations following a priming inoculation with one of the above-listed compositions.

The compositions of the present invention can also be employed to produce an immune response against chronic or latent infectious agents, which typically persist because they fail to elicit a strong immune response in the subject. Illustrative latent or chronic infectious agents include, but are not limited to, hepatitis B, hepatitis C, Epstein-Barr Virus, herpes viruses, human immunodeficiency virus, and human papilloma viruses. Alphavirus replicon particles of this invention encoding peptides and/or proteins from these infectious agents can be administered to a cell or a subject according to the methods described herein.

Alternatively, the immunogenic protein or peptide can be any tumor or cancer cell antigen. Preferably, the tumor or cancer antigen is expressed on the surface of the cancer cell. Exemplary cancer antigens for specific breast cancers are the HER2 and BRCA1 antigens. Other illustrative cancer and tumor cell antigens are described in S.A. Rosenberg, (1999) *Immunity* 10:281) and include, but are not limited to, MART-1/MelanA, gp100, tyrosinase, TRP-1, TRP-2, MAGE-1, MAGE-3, GAGE-1/2, BAGE, RAGE, NY-ESO-1, CDK-4, β-catenin, MUM-1, Caspase-8, KIAA0205, HPVE&, SART-1, PRAME, p15 and p53 antigens, Wilms' tumor antigen, tyrosinase, carcinoembryonic antigen (CEA), prostate specific antigen (PSA), prostate-specific membrane antigen (PSMA), prostate stem cell antigen (PSCA), human aspartyl (asparaginyl) β-hydroxylase (HAAH), and EphA2 (an epithelial cell tyrosine kinase, see International Patent Publication No. WO 01/12172).

The immunogenic polypeptide or peptide of this invention can also be a "universal" or "artificial" cancer or tumor cell antigen as described in international patent publication WO 99/51263, which is incorporated herein by reference in its entirety for the teachings of such antigens.

In various embodiments, the heterologous nucleic acid of this invention can encode an antisense nucleic acid sequence. An "antisense" nucleic acid is a nucleic acid molecule (i.e., DNA or RNA) that is complementary (i.e., able to hybridize in vivo or under stringent in vitro conditions) to all or a portion of a nucleic acid (e.g., a gene, a cDNA and/or mRNA) that encodes or is involved in the expression of nucleic acid that encodes a polypeptide to be targeted for inhibited or reduced production by the action of the antisense nucleic acid. Where the antisense nucleic acid is complementary to a portion of the nucleic acid encoding the polypeptide to be targeted, the antisense nucleic acid should hybridize close enough to the 5' end of the nucleic acid encoding the polypeptide such that it inhibits translation of a functional polypeptide. Typically, this means that the antisense nucleic acid should be complementary to a sequence that is within the 5' half or third of the nucleic acid to which it hybridizes.

An antisense nucleic acid of this invention can also encode a catalytic RNA (i.e., a ribozyme) that inhibits expression of a target nucleic acid in a cell by hydrolyzing an mRNA encoding the targeted gene product. Additionally, hammerhead RNA can be used as an antisense nucleic acid to prevent intron splicing. An antisense nucleic acid of this invention can be produced and tested according to protocols routine in the art for antisense technology.

Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) *Molecular Cloning*, Second Edition, Cold Spring Harbor Laboratory, Plainview, N.Y.; Maniatis et al. (1982) *Molecular Cloning*, Cold Spring Harbor Laboratory, Plainview, N.Y.; Wu (ed.) (1993) *Meth. Enzymol.* 218, Part I; Wu (ed.) (1979) *Meth. Enzymol.* 68; Wu et al. (eds.) (1983) *Meth. Enzymol.* 100 and 101; Grossman and Moldave (eds.) *Meth. Enzymol.* 65; Miller (ed.) (1972) *Experiments in Molecular Genetics*, Cold Spring Harbor Laboratory, Cold Spring Harbor, N.Y.; Old and Primrose (1981) *Principles of Gene Manipulation*, University of California Press, Berkeley; Schleif and Wensink (1982) *Practical Methods in Molecular Biology*; Glover (ed.) (1985) *DNA Cloning* Vol. I and II, IRL Press, Oxford, UK; Hames and Higgins (eds.) (1985) *Nucleic Acid Hybridization*, IRL Press, Oxford, UK; Setlow and Hollaender (1979) *Genetic Engineering: Principles and Methods*, Vols. 1-4, Plenum Press, New York; and Ausubel et al. (1992) *Current Protocols in Molecular Biology*, Greene/Wiley, New York, N.Y., and in other sources referenced herein. Abbreviations and nomenclature, where employed, are deemed standard in the field and commonly used in professional journals such as those cited herein.

All references cited in the present application are incorporated by reference herein to the extent that there is no inconsistency with the present disclosure.

When a Markush group or other grouping is used herein, all individual members of the group and all combinations and subcombinations possible of the group are intended to be individually included in the disclosure. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device in the specification or claims, can be exchanged with "consisting essentially of" or "consisting of".

One of ordinary skill in the art will appreciate that methods, techniques, procedures, e.g., collection and/or purification techniques or procedures, starting materials, culture media, and reagents other than those specifically exemplified can be employed in the practice of the invention without resort to undue experimentation. All art-known functional equivalents, of any such methods, techniques, procedures, starting materials, culture media, and reagents are intended to be included in this invention.

Although the description herein contains many specific recitations and examples, these should not be construed as limiting the scope of the invention, but as merely providing illustrations of some of the embodiments of the invention. All references cited herein are hereby incorporated by reference to the extent that there is no inconsistency with the disclosure of this specification. Some references provided herein are incorporated by reference herein to provide details concerning additional starting materials, additional methods of synthesis, additional methods of analysis and additional uses of the invention.

The following examples are provided for illustrative purposes, and are not intended to limit the scope of the invention as claimed herein. Any variations in the exemplified articles which occur to the skilled artisan are intended to fall within the scope of the present invention.

EXAMPLES

Example 1

Production of TC-83 Replicons

A replicon plasmid based on the TC-83 strain of VEE was produced from a TC-83 infectious cDNA clone, pVE/IC-92, obtained from the Centers for Disease Control and Prevention. The sequence of this clone was published by Kinney et al. (1993) *J. Virol.* 67:1269. The pVE/IC-92 sequence differs from the TC-83 virus genomic sequence by the presence of an Ala-Val mutation at E1-119 (a cloning artifact introduced by Kinney) and three silent mutations in nsp1 (at 1613A→G; at 1616C→A; at 1619T→C) purposely introduced to distinguish the clone-derived virus from the genomic sequence. The present inventors have identified an additional silent mutation at E1 position in the pVE/IC-92 clone. By "silent" is meant that the change in the nucleic acid sequence does not cause a change in the amino acid that is encoded by that nucleic acid sequence.

The TC-83 replicon vector ("pVEK") was produced by first transferring an expressible sequence encoding kanamycin resistance ("KN(R)") into the TC-83 full-length clone to create pVEK/IC-92. A multiple cloning site was inserted in place of the TC-83 structural protein genes by digesting an existing VEE replicon (such as the pERK plasmid, see U.S. Patent Publication No. 2002-141975, Example 2), which has the VEE 26S promoter and 3' UTR (untranslated region), with ApaI and NotI restriction enzymes and ligating that fragment into the same sites of pVEK/IC-92. The resulting plasmid is replicated in bacteria using the COLE1 origin of replication (ORI) and contains the TC-83 5' and 3' UTR's, TC 83 nonstructural protein (nsP) sequences, a VEE 26S promoter, and a multiple cloning site, all placed downstream of a T7 polymerase promoter for in vitro RNA transcription.

Alternatively, the structural proteins of the TC-83 clone were replaced with a chimeric heterologous gene, e.g. either the HIV gag (GAG) gene, the gene encoding the green fluorescent protein (GFP), or an alphavirus (VEE, EEE or WEE) glycoprotein polyprotein sequence.

A second TC-83 based replicon was produced in which the VEE 26S promoter drives transcription of the heterologous gene, while an internal ribosome entry site (IRES) was inserted downstream of the promoter is used to direct translation from the subgenomic RNA (herein referred to as an "IRES replicon" and specifically "VEETC83IRES"). This replicon was generated from pERK-342EnGGAG (herein also referred to as "VEE3000IRES"), which is a wild-type VEE-based replicon that contains a 342 bp sequence (SEQ ID NO:1) (an AluI fragment from the digestion of pcDNA3.1 DNA; Invitrogen, Inc; Carlsbad, Calif.) inserted at the EcoRV restriction enzyme site of pERK between the subgenomic promoter and EMCV IRES, as an ApaI-SphI fragment into pVEK-IC92. The 342 bp sequence is inserted to insure that the IRES is the control element for translation, and has the following sequence:

```
CTATTCCAGAAGTAGTGAGGAGGCTTTTTTGGAGGCCTAGGCTTTTGCAA
AAAGCTTGTATATCCATTTTCGGATCTGATCAAGAGACAGGATGAGGATC
GTTTCGCATGATTGAACAAGATGGATTGCACGCAGGTTCTCCGGCCGCTT
GGGTGGAGAGGCTATTCGGCTATGACTGGGCACAACAGACAATCGGCTGC
TCTGATGCCGCCGTGTTCCGGCTGTCAGCGCAGGGGCGCCCGGTTCTTTT
TGTCAAGACCGACCTGTCCGGTGCCCTGAATGAACTGCAGGACGAGGCAG
CGCGGCTATCGTGGCTGGCCACGACGGGCGTTCCTTGCGCAG
```

The cloning was done in two steps due to the presence of an ApaI restriction enzyme site in the EMCV IRES.

Replicon plasmids were produced by transforming *E. coli* with the plasmid and then isolating the DNA plasmid using a Marligen Biosciences (Ijamsville, Md.) High Purity Plasmid Purification System, which uses a proprietary ion exchange resin to yield highly purified plasmid DNA. Alternatively, another DNA purification procedure that results in DNA which is free of RNA, protein or endotoxin is acceptable.

Aliquots of the purified replicon plasmid were transcribed in vitro from NotI linearized plasmid DNA using T7 polymerase. Typically, the T7 RiboMAX Express System (Promega, Madison, Wis.), which contains a mixture of T7 RNA polymerase, Recombinant RNasin® RNase Inhibitor and yeast inorganic pyrophosphatase that allows for large scale RNA production, was used. The resulting RNA was then purified using the RNeasy Midi kit (Qiagen, Valencia, Calif.), which utilizes a silica-gel-based membrane to bind RNA and purify it away from contaminating protein. Alternatively, another RNA purification scheme which results in purified RNA in water that is free of RNases is acceptable.

Example 2

Production of TC-83 Helpers

A. DNA Helper

A TC-83 DNA helper was constructed from pcDNA-VSp, which is described in U.S. Patent Publication No. 2003-0119182, Example 5. pcDNA-VSp is a DNA helper in which the VEE3014 VEE structural proteins are expressed directly from a CMV promoter. The glycoprotein gene sequence containing the TC-83 mutations was digested from pVE/IC-92 using SpeI and ScaI restriction enzymes, and ligated into pcDNA-Vsp which has been digested with the same enzymes. The introduced mutation at E1-119, which was noted but uncorrected by Kinney et al. (1993) J. Virol. supra as an artifact of the cDNA cloning to produce VE/IC-92, was repaired using the quick change site-directed mutagenesis kit (Stratagene, LaJolla, Calif.) and primers TC83E1119F (GCCTTGCGGATCATGCTGAAGCATATAAAGCGC) (SEQ ID NO:2) and TC83E1119R (GCGCTTTATATGCTTCAGCATGATCCGCAAGGC) (SEQ ID NO:3) to generate pcDNA-TC83r.

*E. coli* cultures transformed with the DNA helper plasmids were sent to Puresyn, Inc. (Malvern, PA) where they were grown up and the resulting DNA was purified using their POLYFLO® technology (ion-paired, reverse phase chromatography resin, Puresyn, Inc., Malvern, PA), resulting in a DNA preparation that was at least 5 mg/ml and free of detectable RNA, ssDNA, linear plasmid or chromosomal DNA.

B. RNA Helpers

The VEE strain TC-83 ("VEETC83") does not contain any amino acid mutations in the capsid structural protein, so a TC-83 capsid helper can be constructed from any VEE strain, e.g. as described in Pushko et al. 1997 and in U.S. Pat. Nos. 5,792,462; 6,156,558; 5,811,407; and 6,008,035. The TC83 glycoprotein helpers were constructed from pcDNA-TC83r, (described above) by digesting with SpeI and NdeI and cloning into a VEE glycoprotein helper RNA (described in the above references and in U.S. Patent Publication No. 2002-0141975, Example 4, incorporated herein by reference) that has been digested with the same enzymes to remove the 3014 glycoprotein sequence, leaving the 5' and 3' sequences. In certain embodiments, an additional mutation at E1 81 (from Phe to Ile) was engineered into the TC-83 glycoprotein helper by site-directed mutagenesis, referred to herein as "GP-E181I".

Each helper plasmid was in vitro transcribed from Not I linearized plasmid DNA using T7 polymerase, exactly as described for the replicon plasmids above.

Example 3

Packaging of TC-83 Replicon with Various Helpers

VEETC83 replicon particles (VRPs) were produced by co-electroporation of a TC83 replicon RNA (expressing the HIV GAG gene), and one or more helper nucleic acids (see Table 1) into Vero cells. Following electroporation, the cells were seeded into 2 T300 flasks containing OPTIPRO® (serum-free culture medium, Gibco, Carlsbad, CA) and incubated for approximately 18 hours. The media was removed from each flask, and 10 ml of a 0.5 M salt wash solution in 10 mM sodium phosphate buffer was added to each flask and incubated for approximately 5 minutes at room temperature before collection and filtration. VRP were titered by incubating serial dilutions of the salt wash and/or the collected medium on Vero cells in 96 well plates overnight at 37° C. and 5% $CO_2$. GAG VRP infected cells were detected using an anti-GAG indirect immunofluorescence assay on Vero cells fixed with MeOH, and titers were determined by counting GAG positive cells at a specific dilution. Similarly, GFP-VRP titers were determined by counting the number of GFP positive cells at a specific dilution under a UV microscope. The results are shown in Table 1.

TABLE 1

| Helper(s) | Replicon | Electroporation Conditions | Inserted RNA encoding: | Total VRP Yield (Salt wash) |
|---|---|---|---|---|
| VEE3014 two RNA helpers (C, GP) | VEE3000 | 4 pulses at 580 V; 25 μF | GAG | 3.11e10 |
| VEE3014 two RNA helpers (C, GP) | VEE3000 | 4 pulses at 580 V; 25 μF | GFP | 2.13e10 |
| VEE3014 two RNA helpers (C, GP) | VEETC83 | 4 pulses at 580 V; 25 μF. | GAG | 2.94e10 |
| VEE3014 two RNA helpers (C, GP) | VEETC83 | 4 pulses at 580 V; 25 μF. | GFP | 1.41e10 |
| pCDNA-TC83r | VEE3000 | 1 pulse at 250 V; 950 μF | GAG | 1.2e9 |
| pCDNA-TC83r | VEETC83 | 1 pulse at 250 V; 950 μF | GAG | 9.6e8 |
| VEETC83 two RNA helpers (C, GP) | VEE3000 | 4 pulses at 580 V; 25 μF. | GAG | 5.98e10 |
| VEETC83 two RNA helpers (C, GP) | VEETC83 | 4 pulses at 580 V; 25 μF. | GAG | 1.15e11 |
| VEETC83 two RNA helpers (C, GP) | VEE3000IRES** | 4 pulses at 580 V; 25 μF. | GAG | 2.85e10 |
| VEE TC-83 two RNA helpers (C, GP) | VEETC83IRES** | 4 pulses at 580 V; 25 μF. | GAG | 3.43e10 |
| VEE TC-83 two RNA helpers (C, GP) | VEETC83IRES** | 4 pulses at 580 V; 25 μF. | GAG | 1.6e10 |
| VEE TC-83 two RNA helpers (C, GP-E181I) | VEETC83IRES** | 4 pulses at 580 V; 25 μF. | GAG | 2.4e9 |

** IRES = contains replicon in which translation of heterologous gene is under the control of an IRES Example 4

A. Packaging of VEETC83 Replicons Expressing Various Heterologous Alphavirus Glycoprotein Genes with TC-83 Structural Proteins Replicons expressing various heterologous nucleic acids were packaged using a single TC-83 DNA helper expressing the entire alphavirus structural polyprotein from the TC-83 strain. In this example, the heterologous genes were glycoprotein cassettes from other alphaviruses. Also included were TC-83 replicons expressing VEE glycoproteins from either the TC-83 or 3014 strain. In each of these constructs, the glycoprotein-encoding heterologous nucleic acid comprises the E3-E2-6k-E1 polyprotein from the respective virus. The glycoprotein cassettes are identified as follows: “WEE CBA87”, from Western equine encephalitis virus strain Cba 87 and “EEE4002” from Eastern equine encephalitis virus strain Florida 91.

For the WEE cassette, the nucleotide sequence of the WEE virus glycoprotein genes (strain Cba 87) was cloned into the TC-83 replicon, starting from the amino-terminal serine codon of E3 through to the carboxy terminal arginine codon of E1 (SEQ ID NO:4), as follows:

```
TCACTAGTTACAGCGCTGTGCGTGCTTTCGAATGTCACATTCCCTTGCGA
CAAACCACCCGTGTGCTATTCACTGGCGCCAGAACGAACACTCGACGTGC
TCGAGGAGAACGTCGACAATCCAAATTACGACACGCTGCTGGAGAACGTC
TTGAAATGTCCATCACGCCGGCCCAAACGAAGCATTACCGATGACTTCAC
GCTGACCAGTCCCTACCTGGGGTTCTGCCCGTATTGCAGACACTCAGCGC
CATGTTTTAGCCCAATAAAAATTGAGAACGTGTGGGACGAATCTGATGAT
GGGTCGATTAGAATCCAGGTCTCGGCACAATTCGGCTACAATCAGGCAGG
CACTGCAGACGTCACCAAGTTCCGGTACATGTCTTACGACCACGACCATG
ACATCAAGGAAGACAGTATGGAGAAATTAGCTATTAGTACATCCGGACCA
TGCCGTCGTCTTGGCCACAAAGGGTACTTCCTGTTAGCTCAATGTCCTCC
AGGTGACAGTGTAACCGTCAGTATCACGAGCGGAGCATCTGAGAATTCAT
GCACCGTGGAGAAAAAGATCAGGAGGAAGTTTGTCGGTAGAGAGGAGTAC
TTGTTCCCACCTGTCCATGGAAAGCTGGTAAAGTGCCACGTTTACGATCA
CTTGAAGGAGACGTCTGCCGGATATATAACTATGCACAGGCCAGGCCCAC
ACGCGTATAAGTCCTACCTGGAGGAAGCGTCAGGCGAAGTGTACATTAAA
CCACCTTCTGGCAAGAACGTCACCTACGAATGTAAGTGTGGTGACTACAG
CACAGGTATTGTGAGCACGCGAACGAAGATGAACGGCTGCACTAAAGCAA
AACAATGCATTGCCTACAAGCGCGACCAAACGAAATGGGTCTTCAACTCG
CCGGATCTTATTAGGCACACAGACCACTCAGTGCAAGGTAAACTGCACAT
TCCATTCCGCTTGACACCGACAGTCTGCCCGGTTCCGTTAGCTCACACGC
CTACAGTCACGAAGTGGTTCAAAGGCATCACCCTCCACCTGACTGCAACG
CGACCAACATTGCTGACAACGAGAAAATTGGGGCTGCGAGCAGACGCAAC
AGCAGAATGGATTACGGGGACTACATCCAGGAATTTTTCTGTGGGGCGAG
AAGGGCTGGAGTACGTATGGGGCAACCATGAACCAGTCAGAGTCTGGGCC
CAGGAGTCGGCACCAGGCGACCCGCATGGATGGCCGCATGAGATCATCAT
CCATTATTATCATCGGCATCCAGTCTACACTGTCATTGTGCTGTGCGGTG
TCGCTCTGGCTATCCTGGTAGGCACTGCATCGTCAGCAGCTTGTATCGCC
AAAGCAAGAAGAGACTGCCTGACGCCATACGCGCTTGCACCGAACGCAAC
GGTACCCACAGCATTAGCAGTTTTGTGCTGTATTCGGCCAACCAACGCTG
AAACATTTGGAGAAACTTTGAACCATCTGTGGTTTAACAACCAACCGTTT
CTCTGGGCACAGTTGTGCATCCCTCTGGCAGCGCTTATTATTCTGTTCCG
CTGCTTTTCATGCTGCATGCCTTTTTTATTGGTTGCAGGCGTCTGCCTGG
GGAAGGTAGACGCCTTCGAACATGCGACCACTGTGCCAAATGTTCCGGGG
ATCCCGTATAAGGCGTTGGTCGAACGTGCAGGTTACGCGCCACTTAATCT
```

-continued

```
GGAGATTACGGTCGTCTCATCGGAATTAACACCCTCAACTAACAAGGAGT
ACGTGACCTGCAAATTTCACACAGTCGTTCCTTCACCACAAGTTAAATGC
TGCGGGTCCCTCGAGTGTAAGGCATCCTCAAAAGCGGATTACACATGCCG
CGTTTTTGGCGGTGTGTACCCTTTCATGTGGGGAGGCGCACAGTGCTTCT
GTGACAGTGAGAACACACAACTGAGTGAGGCATACGTCGAGTTCGCTCCA
GACTGCACTATAGATCATGCAGTCGCACTAAAAGTTCACACAGCTGCTCT
GAAAGTCGGCCTGCGTATAGTATACGGCAATACCACAGCGCGCCTGGATA
CATTCGTCAACGGCGTCACACCAGGTTCCTCACGGGACCTGAAGGTCATA
GCAGGGCCGATATCAGCAGCTTTTTCACCCTTTGACCATAAGGTCGTCAT
TAGAAAGGGGCTTGTTTACAACTACGACTTCCCTGAGTATGGAGCTATGA
ACCCAGGAGCGTTCGGCGATATTCAAGCATCCTCTCTTGATGCCACAGAC
ATAGTAGCCCGCACCGACATACGGCTGCTGAAGCCTTCTGTCAAGAACAT
CCACGTCCCCTACACCCAAGCAGTATCAGGGTATGAAATGTGGAAGAACA
ACTCAGGACGACCCCTGCAAGAAACAGCACCATTCGGATGTAAAATTGAA
GTGGAGCCTCTGCGAGCGACTAACTGTGCTTATGGGCACATCCCTATCTC
GATTGACATCCCTGATGCAGCTTTTGTGAGATCATCTGAATCACCAACAA
TTTTAGAAGTCAGCTGCACAGTAGCAGACTGCATTTATTCTGCAGACTTT
GGTGGTTCGCTAACACTACAGTACAAAGCTAACAGAGAGGGACATTGTCC
AGTTCACTCCCACTCCACTACAGCTGTTTTGAAGGAAGCGACCACACATG
TGACTGCCACAGGCAGCATAACACTACATTTTAGCACATCGAGCCCACAA
GCAAATTTCATAGTTTCGCTATGCGGCAAGAAGACCACCTGCAATGCTGA
ATGTAAACCACCGGCCGACCACATAATTGGAGAACCACATAAGGTCGACC
AAGAATTCCAGGCGGCAGTTTCCAAAACATCTTGGAACTGGCTGCTTGCA
CTGTTTGGGGGAGCATCATCCCTCATTGTTGTAGGACTTATAGTGTTGGT
CTGCAGCTCTATGCTTATAAACACACGTAGA
```

For the EEE cassette, the nucleotide sequence of the EEE virus glycoprotein genes (strain Florida 91) was cloned into the TC-83 replicon, starting from the amino-terminal serine codon of E3 through to the carboxy-terminal histidine codon of E1 (SEQ ID NO:5), as follows:

```
TCGCTCGCCACTGTTATGTGCGTCCTGGCCAATATCACGTTTCCATGTGA
TCAACCACCCTGCATGCCATGCTGTTATGAAAAGAATCCACACGAAACAC
TCACCATGCTGGAACAGAATTACGACAGCCGAGCCTATGATCAGCTGCTC
GATGCCGCTGTGAAATGTAATGCTAGGAGAACCAGGAGAGATTTGGACAC
TCATTTCACCCAGTATAAGTTGGCACGCCCGTATATTGCTGATTGCCCTA
ACTGTGGGCATAGTCGGTGCGACAGCCCTATAGCTATAGAAGAAGTCAGA
GGGGATGCGCATGCAGGAGTCATCCGCATCCAGACATCAGCTATGTTCGG
TCTGAAGACGGATGGAGTCGATTTGGCCTACATGAGTTTCATGAACGGCA
AAACGCAGAAATCAATAAAGATCGACAACCTGCATGTGCGCACCTCAGCC
CCTTGTTCCCTCGTGTCGCACCACGGCTATTACATCTTGGCTCAATGCCC
ACCAGGGGACACGGTTACAGTTGGGTTTCACGACGGGCCTAACCGCCATA
```

-continued

CGTGCACAGTTGCCCATAAGGTAGAATTCAGGCCAGTGGGTAGAGAGAAA

TACCGTCACCCACCTGAACATGGAGTTGAACTACCGTGTAACCGTTACAC

TCACAAGCGTGCAGACCAAGGACACTATGTTGAGATGCATCAACCAGGGC

TAGTTGCCGACCACTCTCTCCTTAGCATCCACAGTGCCAAGGTGAAAATT

ACGGTACCGAGCGGCGCCCAAGTGAAATACTACTGCAAGTGTCCAGATGT

ACGAGAGGGAATTACCAGCAGCGACCATACAACCACCTGCACGGATGTCA

AACAATGCAGGGCTTACCTGATTGACAACAAGAAATGGGTGTACAACTCT

GGAAGACTGCCTCGAGGAGAGGGCGACACTTTTAAAGGAAAACTTCATGT

GCCCTTTGTGCCTGTTAAGGCCAAGTGCATCGCCACGCTGGCACCGGAGC

CTCTAGTTGAGCACAAACACCGCACCCTGATTTTACACCTGCACCCGGAC

CATCCGACCTTGCTGACGACCAGGTCACTTGGAAGTGATGCAAATCCAAC

TCGACAATGGATTGAGCGACCAACAACTGTCAATTTCACAGTCACCGGAG

AAGGGTTGGAGTATACCTGGGGAAACCATCCACCAAAAAGAGTATGGGCT

CAAGAGTCAGGAGAAGGGAACCCACATGGATGGCCGCACGAAGTGGTAGT

CTATTACTACAACAGATACCCGTTAACCACAATTATCGGGTTATGCACCT

GTGTGGCTATCATCATGGTCTCTTGTGTCACATCCGTGTGGCTCCTTTGC

AGGACTCGCAATCTTTGCATAACCCCGTATAAACTAGCCCCGAACGCTCA

AGTCCCAATACTCCTGGCGTTACTTTGCTGCATTAAGCCGACGAGGGCAG

ACGACACCTTGCAAGTGCTGAATTATCTGTGGAACAACAATCAAAACTTT

TTCTGGATGCAGACGCTTATCCCACTTGCAGCGCTTATCGTATGCATGCG

CATGCTGCGCTGCTTATTTTGCTGTGGGCCGGCTTTTTTACTTGTCTGCG

GCGCCTTGGGCGCCGCAGCGTACGAACACACAGCAGTGATGCCGAACAAG

GTGGGGATCCCGTATAAAGCTTTAGTCGAACGCCCAGGTTATGCACCCGT

TCATCTACAGATACAGCTGGTTAATACCAGGATAATTCCATCAACTAACC

TGGAGTACATCACCTGCAAGTACAAGACAAAAGTGCCGTCTCCAGTAGTG

AAATGCTGCGGTGCCACTCAATGTACCTCCAAACCCCATCCTGACTATCA

GTGTCAGGTGTTTACAGGTGTTTACCCATTCATGTGGGGAGGAGCCTACT

GCTTCTGCGACACCGAAAACACCCAGATGAGCGAGGCGTATGTAGAGCGC

TCGGAAGAGTGCTCTATCGACCACGCAAAAGCTTATAAAGTACACACAGG

CACTGTTCAGGCAATGGTGAACATAACTTATGGGAGCGTCAGCTGGAGAT

CTGCAGATGTCTACGTCAATGGTGAAACTCCCGCGAAAATAGGAGATGCC

AAACTCATCATAGGTCCACTGTCATCTGCGTGGTCCCCATTCGATAACAA

GGTGGTGGTTTATGGGCATGAAGTGTATAATTACGACTTTCCTGAGTACG

GCACCGGCAAAGCAGGCTCTTTTGGAGACCTGCAATCACGCACATCAACC

AGCAACGATCTGTACGCAAACACCAACTTGAAGCTACAACGACCCCAGGC

TGGTATCGTGCACACACCTTTCACCCAGGCGCCCTCTGGCTTCGAACGAT

GGAAAAGGGACAAAGGGGCACCGTTGAACGACGTAGCCCCGTTTGGCTGT

TCGATTGCCCTGGAGCCGCTCCGTGCAGAAAATTGTGCAGTGGGAAGCAT

CCCTATATCTATAGATATACCCGATGCGGCTTTCACTAGAATATCTGAAA

CACCGACAGTCTCAGACCTGGAATGCAAAATTACGGAGTGTACTTATGCC

TCCGATTTCGGTGGTATAGCCACCGTTGCCTACAAATCCAGTAAAGCAGG

AAACTGTCCAATTCATTCTCCATCAGGTGTTGCAGTTATTAAAGAGAATG

ACGTCACCCTTGCTGAGAGCGGATCATTTACATTCCACTTCTCCACTGCA

AACATCCATCCTGCTTTTAAGCTGCAGGTCTGCACCAGTGCAGTTACCTG

CAAAGGAGATTGCAAGCCACCGAAAGATCATATCGTCGATTATCCAGCAC

AACATACCGAATCCTTTACGTCGGCGATATCCGCCACCGCGTGGTCGTGG

CTAAAAGTGCTGGTAGGAGGAACATCAGCATTTATTGTTCTGGGGCTTAT

TGCTACAGCAGTGGTTGCCCTAGTTCTGTTCTTCCATAGACAT

TC-83-VEE replicon particles (VRPs) were produced by co-electroporation of replicon RNA (expressing the indicated alphavirus glycoprotein polyprotein), and the single DNA helper encoding the TC-83 structural proteins into $10^8$ Vero cells. Following electroporation, the cells were seeded into 2 T300 flasks containing OPTIPRO® SFM (serum-free culture medium, Gibco, Carlsbad, CA) and incubated for approximately 18 hours. The media was then removed from the flask, and 10 mls of a 0.5 M salt wash solution in 10 mM sodium phosphate buffer was added to each flask and incubated for approximately 5 minutes at room temperature before collection and filtration. VRP were titered by incubating serial dilutions of the collected VRP on Vero cells in 96 well plates overnight at 37° C. and 5% $CO_2$. Alphavirus glycoprotein-expressing VRP infected cells were detected using an anti-WEE, anti-VEE, or anti-EEE indirect immunofluorescence assay on Vero cells fixed with 1:1 Acetone:MeOH, and titers were determined by counting antigen-positive cells at a specific dilution. The results are shown in Table 2.

TABLE 2

| TC-83 Replicon ("pVEK") expressing: | Total VRP Yield |
|---|---|
| WECBA87 | $3.4 \times 10^9$ |
| EE4002 | $4.3 \times 10^8$ |
| VEE-3014 | $2.0 \times 10^9$ |
| VEE-TC83 | $3.8 \times 10^9$ |

B. Packaging of VEETC83 and Wild-type VEE Replicons Expressing a Gene from SARS with VEETC83 or VEE3014 Structural Proteins The S2 glycoprotein gene from the Severe Acute Respiratory Syndrome virus ("SARS-S2") was PCR amplified from a SARS coronavirus capsid clone (Urbani strain of SARS coronavirus; Accession # AY278741; obtained from the United States Centers for Disease Control and Prevention, Atlanta, Ga.) and inserted into a pERK replicon (described in Example 1 above) as a BamHI restriction fragment immediately downstream of the enterovirus 71 (EV71) IRES. This replicon, capable of expressing the SARS-S2 glycoprotein gene, was packaged into VRPs using either 3014 or TC83 structural proteins. The structural proteins were expressed either from two separate RNA helpers or from a single DNA helper. For the split RNA helper approach, 30 μg replicon RNA was combined with 30 μg each of the VEE capsid RNA helper and the VEE glycoprotein helper (either from VEE3014 or VEETC83, see Example 2B above) and co-electroporated into $1.2\times10^8$ Vero cells. In this experiment, electroporation was carried out in 0.4 cm gap cuvettes using four pulses, each at 580V and 25 μF. For packaging with a single DNA helper (encoding the entire sequence of either the VEETC83 structural polyprotein or the VEE3014 structural polyprotein), 30 μg replicon RNA was combined with 150 μg of the DNA helper and co-electroporated into $1.2\times10^8$ Vero cells in a 0.4 cm gap cuvette, using a single pulse at 250V and 950 μF. VRPs were produced, harvested and tittered as described in Example 3A, and the yields on a per cell basis are reported in Table 3. The yield per cell of VRPs using TC-83 glycoprotein helpers (as described earlier, the capsid sequence is the same in both VEETC83 and VEE3014), whether in the RNA or DNA helper format, was nearly 4 times greater than the yield recovered with 3014 glycoprotein helpers.

TABLE 3

SARS-S2 VRP yields from cells electroporated with RNA vs. DNA helpers expressing the VEE3014 or VEETC83 glycoprotein genes.

| EP# | Helper #1 | Helper #2 (amt used) | IU/Cell |
|---|---|---|---|
| 1 | Capsid RNA | VEE3014 GP RNA | 1000 |
| 2 | Capsid RNA | VEETC83 GP RNA | 4000 |
| 3 | pCDNA-VSp | NA | 51 |
| 4 | pCDNA-VSp | NA | 44 |
| 5 | pCDNA-VSp | NA | 77 |
| 6 | pCDNA-TC83r | NA | 260 |
| 7 | pCDNA-TC83r | NA | 230 |
| 8 | pCDNA-TC83r | NA | 290 |

C. Enhanced Yield of VRPs Using a VEETC83 DNA Helper

The experiment in 3B. indicated that the VEETC83 DNA helper was associated with higher yields of VRPs (compare EP#3-5 with EP#6-8). This was confirmed in a second set of experiments, in which replicon RNAs expressing either the GAG gene or GFP were packaged with either pcDNA-TC83r or the pcDNA-VSp helper (see Table 4). These studies also confirmed that the solution in which the DNA helper was resuspended prior to co-electroporation (e.g. water ($H_2O$), phosphate buffered saline (PBS) or Tris EDTA (10 mM Tris-HCl, 1 mM EDTA, pH 8.0) does not significantly affect yield, even if the DNA is stored for many months (e.g. 1, 3, 4, 5 or 6 months) at −20° C.

TABLE 4

VRP yields from VEETC83 DNA helper vs. VEE3014 DNA helper

| EP# | Replicon (amount used) | Helper (amt used) | IU/Cell |
|---|---|---|---|
| 1 | VEE3000/GFP (30 μg) | pCDNA-VSp ($H_2O$) (150 μg) | 43 |
| 2 | VEE3000/GFP (30 μg) | pCDNA-VSp (PBS) (150 μg) | 23 |
| 3 | VEE3000/GFP (30 μg) | pCDNA-VSp (TE) (150 μg) | 51 |
| 4 | VEE3000/GFP (30 μg) | pCDNA-TC83r ($H_2O$) (150 μg) | 130 |
| 5 | VEE3000/GFP (30 μg) | pCDNA-TC83r (PBS) (150 μg) | 100 |
| 6 | VEE3000/GFP (30 μg) | pCDNA-TC83r (TE) (150 μg) | 98 |
| 7 | VEE3000(nt3A)IRES/Gag (30 μg) | pCDNA-VSp ($H_2O$) (150 μg) | 90 |
| 8 | VEE3000(nt3A)IRES/Gag (30 μg) | pCDNA-VSp (PBS) (150 μg) | 60 |
| 9 | VEE3000(nt3A)IRES/Gag (30 μg) | pCDNA-VSp (TE) (150 μg) | 110 |
| 10 | VEE3000(nt3A)IRES/Gag (30 μg) | pCDNA-TC83r ($H_2O$) (150 μg) | 200 |
| 11 | VEE3000(nt3A)IRES/Gag (30 μg) | pCDNA-TC83r (PBS) (150 μg) | 250 |
| 12 | VEE3000(nt3A)IRES/Gag (30 μg) | pCDNA-TC83r (TE) (150 μg) | 300 |
| 13 | VEE3000(nt3A)IRES/Gag (30 μg) | pCDNA-VSp ($H_2O$) (150 μg) | 74 |
| 14 | VEE3000(nt3A)IRES/Gag (30 μg) | pCDNA-VSp (PBS) (150 μg) | 73 |
| 15 | VEE3000(nt3A)IRES/Gag (30 μg) | pCDNA-VSp (TE) (150 μg) | 68 |
| 16 | VEE3000(nt3A)IRES/Gag (30 μg) | pCDNA-TC83r ($H_2O$) (150 μg) | 150 |
| 17 | VEE3000(nt3A)IRES/Gag (30 μg) | pCDNA-TC83r (PBS) (150 μg) | 190 |
| 18 | VEE3000(nt3A)IRES/Gag (30 μg) | pCDNA-TC83r (TE) (150 μg) | 200 |

Example 5

Heparin Affinity Chromatography of TC-83 VRPs

Figure 2:
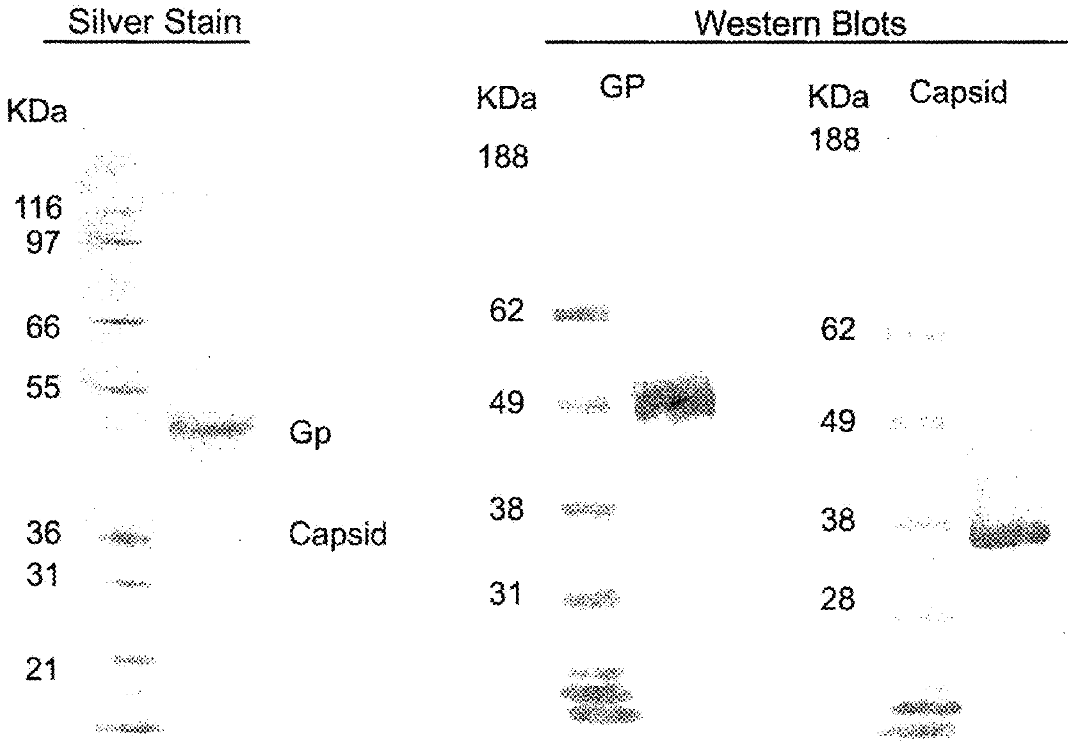
FIG. 2 shows the results of SDS-PAGE of TC-83 virus replicon particles after heparin affinity chromatography, with the proteins visualized by silver staining and by Western blotting using capsid-specific and glycoprotein-specific antibodies and staining.
Figure 3:
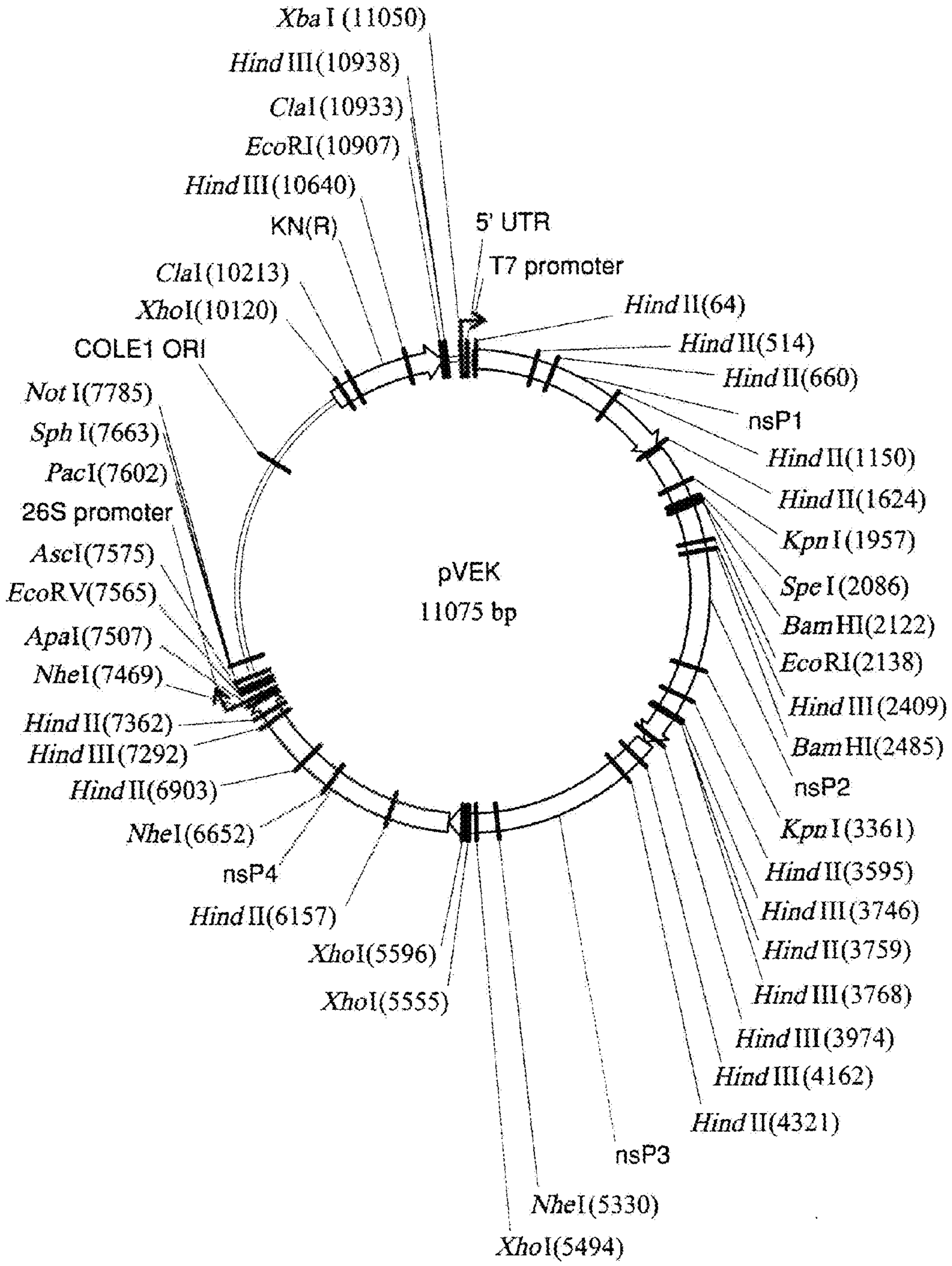
FIG. 3 is a plasmid map of the TC-83 replicon cloning vector pVEK.

TC-83 VRPs, collected from Vero cells via a 1 M salt wash of the cells, were diluted with 16 mM sodium phosphate (SP) pH 7.4 to a sodium chloride concentration of 0.12 M or less. The solution was then loaded onto a column containing Heparin sepharose fast flow resin (Amersham) at a linear velocity of 5 ml/min. The TC-83 VRPs were eluted with a linear gradient of increasing sodium chloride concentration (approximately 120 mM to 1 M). The TC-83 VRPs elute at a sodium chloride concentration of approximately 3 M at a pH of 7.4. FIG. 1 shows the elution profile of TC-83 VRPs purified by this method. The sharp UV peak (between fractions 14 and 23) corresponds to VRP elution. The fractions containing greater then 1e9 VRP (fractions 18-23) were collected from the column and formulated by direct dilution in 1% human serum albumin and 5% sucrose. Prior to formulation, 1e8 infectious units (IU) of purified bulk VRP were fractionated by SDS-PAGE and analyzed by silver stain or western blot using capsid or glycoprotein specific antibodies to assess purity (FIG. 2). In the silver stained gel, only bands corresponding in size to the capsid and glycoproteins are evident, indicating a surprising level of purity.

Example 6

Immunogenicity of TC-83 VRPs

The immunogenicity of TC-83 VRPs has been studied in laboratory animals.

BALB/c mice, five animals per group, were immunized with the indicated VRP particles by subcutaneous inoculation in the footpad at the indicated dose. The animals were immunized three times (at 3-week intervals). Humoral responses were measured by GAG ELISA 7-days after the first and second booster inoculations, and cellular responses were measured by interferon-gamma ELISPOT 7-days after the second booster inoculation. The ELISA and ELISPOT data presented in Table 6 are the geometric and arithmetic means, respectively, calculated from the five mice from each group.

The response to the VEE vector was assessed by a VEE neutralization assay (see below).

TABLE 6

Immunogenicity in Mice, Experiment 1.

| | | Immunogenicity | | |
|---|---|---|---|---|
| | | ELISA (GMT) | | ELISPOT* (SFCs/1 e6 |
| GAG VRP** | Dose | after $1^{st}$ boost | after $2^{nd}$ boost | (lymphocytes) after $2^{nd}$boost |
| VEE3000* | 1 E3 | 6756 | 12177 | 1330 |
| VEE3000* | 1 E4 | 13512 | 27024 | 1203 |
| VEE3000* | 1 E6 | 40960 | 48710 | 1217 |
| VEE3014* | 1 E4 | 46 | 92 | 212 |
| VEE3014* | 1 E6 | 6756 | 17222 | 793 |
| VEETC83 | 1 E4 | 243 | 844 | 284 |
| VEETC83 | 1 E5 | 1940 | 10240 | 542 |
| VEETC83 | 1 E6 | 2941 | 15521 | 1050 |
| VEETC83IRES | 1 E6 | 1940 | 13512 | 449 |
| VEETC83(E181I)IRES | 1 E6 | 8914 | 23525 | 607 |

*The replicons in the 3000 and 3014 VRPs contain a mutation to A at nucleotide 3 of the replicon

**VEE3000 and VEE3014 VRPs are packaged with wild-type (VEE3000) and VEE3014 structural proteins respectively; VEETC83 VRPs contain a TC83-derived replicon RNA that is packaged with TC83 structural proteins To demonstrate that each mouse of each TC-83 treatment group responded with both humoral and cellular immune responses, the ranges for the five responses recorded for each treatment group are presented in the following Table 7:

TABLE 7

Humoral and Cellular Immune Responses (Experiment 1, Mice)

| | | ELISA range | | ELISPOT range |
|---|---|---|---|---|
| GAG VRP Replicon | Dose | Post-boost 1 | Post-boost 2 | Post-boost 2 |
| VEETC83 | 1 e4 | 80-640 | 640-2560 | 173-473 |
| VEETC83 | 1 e5 | 640-2560 | 5120-20480 | 252-838 |
| VEETC83 | 1 e6 | 2560-5120 | 10240-20480 | 724-1577 |
| VEETC83IRES | 1 e6 | 1280-5120 | 5120-40960 | 202-723 |
| VEETC83(E181I)IRES | 1 e6 | 5120-10240 | 10240-40960 | 269-880 |
| VEE3014IRES | 1 e6 | 2560-5120 | 10240-20480 | 609-933 |

TABLE 8

Humoral and Cellular Responses (Experiment 2, mice)

| | | | Immunogenicity | | |
|---|---|---|---|---|---|
| | | | ELISA (GMT) | | ELISPOT* (SFCs/1 e6 (lymphocytes) |
| GAG VRP VEE strain | Route | Dose | after $1^{st}$ boost | after $2^{nd}$ boost | after $2^{nd}$ boost |
| 3014IRES*** | footpad | 1e6 | 10240 | 37924 | 910 |
| 3014IRES | footpad | 1e7 | 13512 | 70225 | 970 |
| 3014IRES | footpad | 5e7 | 20480 | 67202 | 1529 |
| TC-83IRES | footpad | 1e6 | 3378 | 11763 | 654 |
| TC-83IRES | footpad | 1e7 | 8127 | 27869 | 787 |
| TC-83IRES | footpad | 5e7 | 9554 | 37924 | 951 |
| TC-83(E181-I)IRES | footpad | 1e6 | 4389 | 12902 | 713 |
| TC-83(E181-I)IRES | footpad | 1e7 | 6640 | 30433 | 1121 |
| TC-83(E181-I)IRES | footpad | 5e7 | 10240 | 36491 | 872 |

TABLE 8-continued

Humoral and Cellular Responses (Experiment 2, mice)

| | | | Immunogenicity | | |
|---|---|---|---|---|---|
| | | | ELISA (GMT) | | ELISPOT* (SFCs/1 e6 (lymphocytes) |
| GAG VRP VEE strain | Route | Dose | after $1^{st}$ boost | after $2^{nd}$ boost | after $2^{nd}$ boost |
| TC-83IRES | intra-muscular | 1e6 | 300 | 3335 | 672 |
| TC-83IRES | intra-muscular | 1e7 | 2903 | 6451 | 1877 |
| TC-83IRES | intra-muscular | 5e7 | 4400 | 23525 | 1297 |
| TC-83(E181-I)IRES | intra-muscular | 1e6 | 304 | 1781 | 800 |
| TC-83(E181-I)IRES | intra-muscular | 1e7 | 5881 | 40960 | 1666 |
| TC-83(E181-I)IRES | intra-muscular | 5e7 | 20480 | 54047 | 1023 |

*ELISPOT numbers are averages

**10 animals/group for the footpad injections and 5/group in intramuscular injections

***no nt3 mutation

TABLE 9

Anti-Vector Response (for animals in Table 8)

| | | Anti-Vector Response to GFP VRP (GMT) | |
|---|---|---|---|
| GAG VRP VEE strain | Dose/ Route | after $1^{st}$ boost | after $2^{nd}$ boost |
| 3014IRES* | 1 e6/fp | 320 | 830 |
| 3014IRES | 1 e7/fp | 28963 | 34443 |
| 3014IRES | 5 e7/fp | 40960 | 40960 |
| TC-83IRES | 1 e6/fp | 1 | 1 |
| TC-83IRES | 1 e7/fp | 8 | 274 |
| TC-83IRES | 5 e7/fp | 1576 | 2195 |
| TC-83(E1 81-I)IRES | 1 e6/fp | 1 | 1 |
| TC-83(E1 81-I)IRES | 1 e7/fp | 7 | 640 |
| TC-83(E1 81-I)IRES I | 5 e7/fp | 1114 | 1280 |
| TC-83IRES | 1 e6/im | 1 | 1 |
| TC-83IRES | 1 e7/im | 2 | 9 |
| TC-83IRES | 5 e7/im | 29 | 160 |
| TC-83(E1 81-I)IRES | 1 e6/im | 1 | 1 |
| TC-83(E1 81-I)IRES | 1 e7/im | 3 | 40 |
| TC-83(E1 81-I)IRES | 5 e7/im | 1689 | 2560 |

Primate studies were also carried out. The immunogenicity of a TC-83 replicon vaccine containing the same HIV Glade C gag gene, was conducted in cynomolgus macaques at the Southern Research Institute, Frederick, Md. The construct used in this study was a TC-83 IRES replicon as described above, containing the EMCV IRES, and a 342 nucleotide spacer sequence (see Example 1). Each vaccine was administered to six animals by subcutaneous and intramuscular injection (three animals/route). Animals received three inoculations of $1\times10^8$ vaccine particles at 0, 1 and 6 months. Humoral immune responses to gag were analyzed 2 weeks after each booster inoculation, as well as 20 weeks after the first booster, i.e. prior to the second booster. Anti-vector responses were also measured (see Example 6C). Additional safety data were obtained through clinical chemistries and hematology (hemoglobin, WC, platelet count) which was conducted two weeks after each inoculation.

TABLE 10

Immunization in Primates: ELISA Responses for Cynomolgus Macaques (individual animals):

| Route of Administration | Animal # | ELISA (titer) 2 wk PB1 | 20 wk PB1 | 2 wk PB2 |
|---|---|---|---|---|
| s.c. | 1 | 80 | 10 | 40 |
| s.c | 2 | 10 | 80 | 40 |
| s.c. | 3 | 160 | 10 | 320 |
| i.m. | 4 | 10 | 10 | 320 |
| i.m. | 5 | 640 | 80 | 5120 |
| i.m. | 6 | 640 | 10 | 5120 |

TABLE 11

ELISA GMT (Geometric Mean Titer, Cynomolgus Macaques):

| Route of Administration | 2 wk PB1 GMT | 20 wk PB1 GMT | 2 wk PB2 GMT |
|---|---|---|---|
| Subcutaneous | 50.4 | 20 | 80.0 |
| Intramuscular | 160 | 20 | 2031.9 |

Cellular immunity was also measured in the primate model. Anti-Gag T cell responses in cynomolgus macaques vaccinated with various VRPs (into which the HIV gag coding sequence was expressed) were measured using interferon-gamma ELISPOT assays using pools of overlapping 9mer or 15mer peptides from the HIV Gag protein. Data are presented in Table 12 as the number of positively responding animals/total animals receiving that vaccination protocol. Positively responding animals were defined as those whose responses were greater than 10 spots after background subtraction of the responses to irrelevant peptide pools.

TABLE 12

Anti-Gag T cell responses in Cynomolgus Macaques

| GAG VRP Replicon* | Route | 2 wk PP | 4 wk PP | 2 wk PB1 | 4 wk PB1 | 8 wk PB1 | 24 wk PB1 | 2 wk PB2 | 4 wk PB2 |
|---|---|---|---|---|---|---|---|---|---|
| VEE3014 | s.c. | 1/3 | 0/3 | 1/3 | 1/3 | 1/3 | 0/3 | 1/3 | 0/3 |
| IRES | i.m. | 0/3 | 0/3 | 0/3 | 0/3 | 0/3 | 0/3 | 1/3 | 0/3 |
| VEETC83 | s.c. | 1/3 | 0/3 | 2/3 | 3/3 | 3/3 | 0/3 | 2/3 | 1/3 |
| IRES | i.m. | 1/3 | 0/3 | 2/3 | 1/3 | 1/3 | 1/3 | 2/3 | 1/3 |

PP = post-prime, PB1 = post-boost 1, PB2 = post-boost 2
*Replicon packaged with homologous helper(s)

Macaque T cell responses were also analyzed utilizing intracellular cytokine staining (ICS) analysis, in which cells were purified 6 weeks post-boost 2 and analyzed for IL-2 and IL-4 production in response to Gag overlapping 15mer peptides by ICS. The results are presented in Table 13, where positively responding animals were defined as those whose responses were at least 2 times the response to irrelevant peptide pools.

TABLE 13

ICS Analysis of Vaccinated Macaques.

| GAG VRP | | CD4 | | CD8 | |
|---|---|---|---|---|---|
| Replicon | Route | IL-4 | IL-2 | IL-4 | IL-2 |
| VEE3014 | s.c. | 1/3 | 1/3 | 2/3 | 1/3 |
| IRES | i.m. | 0/3 | 0/3 | 0/3 | 0/3 |

TABLE 13-continued

ICS Analysis of Vaccinated Macaques.

| GAG VRP | | CD4 | | CD8 | |
|---|---|---|---|---|---|
| Replicon | Route | IL-4 | IL-2 | IL-4 | IL-2 |
| VEETC83 | s.c. | 3/3 | 2/3 | 1/3 | 1/3 |
| IRES | i.m. | 2/3 | 0/3 | 0/3 | 0/3 |

The cumulative T cell responses in macaques are summarized in Table 14.

TABLE 14

Summary: Gag specific T cell responses In Macaques

| GAG VRP Replicon | Route | Positive animals/group |
|---|---|---|
| VEE3014 IRES | s.c. | 3/3 |
| | i.m. | 1/3 |
| VEETC83 IRES | s.c. | 3/3 |
| | i.m. | 2/3 |

Humoral immunity was determined using a Gag-specific ELISA (enzyme-linked immunosorbent assay). Purified recombinant histidine-tagged (his)-p55 from HIV-1 subtype C isolate DU-422 (AIDS Res. Hum. Retroviruses. 2003 February; 19(2):133-44) was used as the coating antigen. Briefly, BHK cells were transfected with VEE replicon RNA expressing his-p55, and Triton-X 100 lysates were prepared. Protein was purified by metal ion affinity (nickel) chromatography using a commercially available resin and according to the supplier's instruction.

Murine sera, 7 days post boost, were evaluated for the presence of Gag-specific antibodies by a standard indirect ELISA. For detection of Gag-specific total Ig, a secondary polyclonal antibody that detects IgM, IgG and IgA was used for end point titer determination. Briefly, 96-well Maxisorp ELISA plates (Nunc, Naperville, Ill.) were coated with 50 μl of 0.05 M sodium carbonate buffer, pH 9.6 (Sigma Chemical Co., St. Louis, Mo.) containing 40-80 ng his-p55 per well. Plates were covered with adhesive plastic and incubated overnight at 4° C. The next day, unbound antigen was discarded, and plates were incubated for 1 hour with 200 μl blocking buffer (PBS containing 3% w/v BSA) at room temperature. Wells were washed 6 times with PBS and 50 μl of test serum, diluted serially two-fold in buffer (PBS with 1% w/v BSA and 0.05% v/v Tween 20), was added to antigen-coated wells. Mouse anti-p24 monoclonal antibody (Zeptometrix, Buffalo, N.Y.) was included in every assay as a positive control. Negative controls in each assay included blanks (wells with all reagents and treatments except serum) and pre-bleed sera. Plates were incubated for one hour at room temperature, and then rinsed 6 times with PBS. 50 μl/well of alkaline phosphatase (AP)-conjugated goat anti-mouse poly-isotype secondary antibody (Sigma) diluted to a predetermined concentration in diluent buffer was added to each well and incubated for 1 hour at room temperature. Wells were rinsed 6 times with PBS before addition of 100 μL p-nitrophenyl phosphate (pNPP) substrate (Sigma). The serum antibody ELISA titer was defined as the inverse of the greatest serum dilution giving an optical density at 405 nm greater than or equal to 0.2 above the background (blank wells).

GAG antigen-specific Interferon-gamma (IFN-γ) secreting cells were detected using an IFN-γELISPOT Assay. Single-cell suspensions of splenic lymphocytes from TC-83 VRP-GAG-immunized BALB/c mice were prepared by physical disruption of the splenic capsule in R-10 medium (RPMI medium 1640 supplemented with 100 U/ml penicillin, 100 μg/ml streptomycin, 0.1 mM MEM non-essential amino acids solution, 0.01 M HEPES, 2 mM glutamine and 10% heat inactivated fetal calf serum). Lymphocytes were isolated by Lympholyte M density gradient centrifugation (Accurate Scientific, Westbury, N.Y.), washed twice and resuspended in fresh R-10 medium. Total, unseparated splenic lymphocyte populations were tested.

A mouse IFN γELISPOT kit (Monoclonal Antibody Technology, Nacka, Sweden) was used to perform the assay. Viable cells were seeded into individual ELISPOT wells in a Multiscreen Immobilon-P ELISPOT plate (ELISPOT certified 96-well filtration plate, Millipore, Bedford, Mass.) that had been pre-coated with an anti-IFN-γ monoclonal antibody, and incubated for 16-20 hours. Cells were removed by multiple washes with buffer and the wells were incubated with a biotinylated anti-IFN-γ monoclonal antibody, followed by washing and incubation with Avidin-Peroxidase-Complex (Vectastain ABC Peroxidase Kit, Vector Laboratories, Burlingame, Calif.). Following incubation, the wells were washed and incubated for 4 minutes at room temperature with substrate (Avidin-Peroxidase Complex tablets, Sigma) to facilitate formation of spots, which represent the positions of the individual IFN-γ-secreting cells during culture. Plates were enumerated by automated analysis with a Zeiss KS ELISPOT system.

To enumerate Gag-specific IFN-γ secreting cells in lymphocytes from mice immunized with various VRP constructs expressing gag, lymphocytes were stimulated with the immunodominant CD8H-2$K^d$-restricted HIV-Gag peptide, or an irrelevant CD8H-2$K^d$-restricted Influenza-HA peptide for 16-20 hours (5% $CO_2$ at 37° C.). The peptides were tested at 10 μg/ml and the nef control was tested at 20 μg/ml. Cells minus peptide serve as a background control. As a positive control, cells were stimulated with 4 μg/mL concanavalin A for a similar time period. Peptides were synthesized and purified to >90% at New England Peptide.

C. VEE Neutralization Assay

Neutralizing antibody activity against Venezuelan equine encephalitis (VEE) virus was measured in serum samples of immunized animals (mice or cynomolgus monkeys) using VEE replicon particles (VRP). This test is designed to assess the prevention of productive VRP infection of VRP-susceptible cells by neutralizing antibodies that are present in the serum. In this assay, a defined quantity of propagation-defective VRP expressing green fluorescent protein (GFP) is mixed with serial dilutions of the animal's serum, incubated, and inoculated onto cell monolayers. Following another period of incubation, the cell monolayers are examined for GFP-positive cells under UV light. The infectivity of GFP-expressing VRP ("GFP-VRP") is prevented, or "neutralized", by VEE virus specific neutralizing antibodies in the serum.

The assay is performed as follows: Day 1: Serum from immunized animals (mice or cynomolgus monkeys) is heat inactivated at 56° C. for 30 minutes, and then serially diluted in media (MEM with Earle's Salts and L-glutamine, Invitrogen 11095072, supplemented with 0.1 mM Non-Essential Amino Acids, 100 U/ml penicillin and 100 μg/ml streptomycin). These dilutions are mixed with a defined quantity (between $5\times10^3$ and $1.5\times10^4$) of GFP-VRP and incubated overnight at 4° C. Day 2: 50 μl of the serum:GFP-VRP mixture is added to a 96-well plate of confluent Vero cells and incubated at 37° C. for one hour. The serum:GFP-VRP mixture is removed and replaced with 100 μl of fresh media and incubated overnight at 37° C. Day 3: the number of GFP-positive cells are quantified under UV light. The 80% neutralization level is determined for each sample and is defined as the greatest serum dilution giving a mean GFP-positive cells (GPC) per grid that is less than or equal to 20% of the number of GPCs per grid in control wells infected with GFP-VRP alone or with GFP-VRP pre-incubated with negative control sera (i.e. pre-immunization sera).

TABLE 15

Anti-VEE responses in Mice immunized with GAG-VRP

| GAG VRP VEE strain | Dose | Anti-Vector Response (GMT) after 1st boost | Anti-Vector Response (GMT) after 2nd boost |
|---|---|---|---|
| TC-83 | 1 e4 | 1* | 1 |
| TC-83 | 1 e5 | 1 | 1 |
| TC-83 | 1 e6 | 1 | 1 |
| VEE3014 | 1 e4 | 1 | 1 |
| VEE3014 | 1 e6 | 1 | 32 |
| VEE3000 | 1 e3 | 2 | 2 |
| VEE3000 | 1 e4 | 15 | 70 |
| VEE3000 | 1 e6 | 8914 | 40960 |
| TC-83IRES | 1 e6 | 1 | 1 |
| TC-83(E181I)IRES | 1 e6 | 1 | 1 |
| VEE 3014IRES | 1 e6 | 2 | 36 |

*To calculate GMT anti-vector titers of <1:10 were arbitrarily assigned a value of 1.

TABLE 16

Anti-VEE responses in Cynomolgus monkeys immunized with GAG-VRP

| VEE replicon | #[1] | Rte[2] | 2W[3] PP[4] | 4 W PP | 2 W PB[5] | 4 W PB | 6 W PB | 8 W PB | 12 W PB | 14 W PB | 16 W PB | 20 W PB |
|---|---|---|---|---|---|---|---|---|---|---|---|---|
| TC-83 | 1 | s.c. | ≤10 | ≤10 | 80 | 40 | 40 | 20 | 10 | 10 | 10 | 10 |
| TC-83 | 2 | s.c. | ≤10 | ≤10 | ≤10 | ≤10 | ≤10 | ≤10 | 20 | 40 | 20 | 40 |
| TC-83 | 3 | s.c. | 10 | ≤10 | 160 | 320 | 320 | 320 | 160 | 160 | 160 | 80 |
| TC-83 | 1 | i.m. | ≤10 | ≤10 | ≤10 | ≤10 | ≤10 | 20 | ≤10 | ≤10 | ≤10 | ≤10 |
| TC-83 | 2 | i.m. | ≤10 | ≤10 | ≤10 | 10 | 10 | 40 | ≤10 | 10 | ≤10 | ≤10 |
| TC-83 | 3 | i.m. | ≤10 | ≤10 | ≤10 | 10 | ≤10 | 40 | ≤10 | 20 | ≤10 | ≤10 |
| 3014 | 1 | s.c. | 640 | 640 | 20480 | 10240 | 10240 | 5120 | 1280 | 1280 | 1280 | 1280 |

TABLE 16-continued

Anti-VEE responses in Cynomolgus monkeys immunized with GAG-VRP

| VEE replicon | #[1] | Rte[2] | 2W[3] PP[4] | 4 W PP | 2 W PB[5] | 4 W PB | 6 W PB | 8 W PB | 12 W PB | 14 W PB | 16 W PB | 20 W PB |
|---|---|---|---|---|---|---|---|---|---|---|---|---|
| 3014 | 2 | s.c. | 10 | 10 | 640 | 640 | 1280 | 640 | 160 | 80 | 80 | 160 |
| 3014 | 3 | s.c. | 1280 | 640 | 10240 | 5120 | 5120 | 2560 | 1280 | 1280 | 2560 | 2560 |
| 3014 | 1 | i.m. | 160 | 80 | 40960 | 40960 | 10240 | 5120 | 5120 | 2560 | 2560 | 2560 |
| 3014 | 2 | i.m. | 640 | 40 | 5120 | 10240 | 2560 | 1280 | 640 | 640 | 640 | 320 |
| 3014 | 3 | i.m. | 20 | 10 | 2560 | 5120 | 1280 | 640 | 640 | 320 | 320 | 320 |

[1]animal identification number
[2]route of administration: s.c. = subcutaneous; i.m. = intramuscular
[3]W = week
[4]PP = post-priming inoculation
[5]PB = post-first boosting inoculation

What is claimed is:

1. A method of producing an immune response to an immunogen heterologous to an alphavirus in a subject, comprising administering to the subject an effective amount of a composition comprising infectious, propagation-defective alphavirus particles and a pharmaceutically-acceptable carrier, wherein each particle comprises an alphavirus replicon RNA comprising an alphavirus packaging signal and one or more heterologous RNA sequence(s) encoding an immunogen heterologous to the alphavirus, and wherein said alphavirus replicon RNA lacks sequences encoding alphavirus structural proteins, and wherein each particle comprises structural proteins from Venezuelan equine encephalitis virus TC-83.

2. The method of claim 1, wherein the composition is administered via intramuscular, subcutaneous or intraperitoneal injection.

3. The method of claim 1, wherein the alphavirus replicon RNA is from Venezuelan equine encephalitis virus.

4. The method of claim 1, wherein there is one heterologous RNA sequence or wherein there are two heterologous RNA sequences.

5. A method of producing an immune response in a subject, comprising administering to the subject an effective amount of a composition comprising infectious, propagation-defective alphavirus replicon particles and a pharmaceutically-acceptable carrier, wherein each particle comprises a Venezuelan equine encephalitis (VEE) TC-83-derived alphavirus replicon RNA, said replicon RNA comprising a 5' sequence of VEE strain TC-83 RNA which initiates transcription of alphavirus RNA, one or more nucleotide sequences which together encode TC-83 alphavirus nonstructural proteins necessary for replication of the replicon RNA, an alphavirus packaging signal and one or more heterologous RNA sequence(s) encoding an immunogen heterologous to VEE TC-83, and a 3' RNA polymerase recognition sequence of VEE strain TC-83 wherein said alphavirus replicon RNA lacks sequences encoding alphavirus structural proteins, and wherein each particle comprises structural proteins from Venezuelan equine encephalitis virus TC-83.

6. The method of claim 5, wherein the composition is administered via intramuscular, subcutaneous or intraperitoneal injection.

7. The method of claim 5, wherein there is one heterologous RNA sequence or wherein there are two heterologous RNA sequences in said replicon RNA.

* * * * *